United States Patent [19]
Elsberry et al.

[11] Patent Number: 6,094,598
[45] Date of Patent: *Jul. 25, 2000

[54] METHOD OF TREATING MOVEMENT DISORDERS BY BRAIN STIMULATION AND DRUG INFUSION

[75] Inventors: Dennis D. Elsberry, New Hope; Mark T. Rise, Monticello; Gary W. King, Fridley, all of Minn.

[73] Assignee: Medtronics, Inc., Minneapolis, Minn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/637,534

[22] Filed: Apr. 25, 1996

[51] Int. Cl.$^7$ .............................. A61N 1/05; A61M 5/142
[52] U.S. Cl. ........................... 607/116; 607/117; 607/118
[58] Field of Search ................................... 607/3, 48, 49, 607/116, 117, 118

[56] References Cited

U.S. PATENT DOCUMENTS

| | | |
|---|---|---|
| 4,146,029 | 3/1979 | Ellinwood, Jr. . |
| 4,692,147 | 9/1987 | Duggan . |
| 5,002,053 | 3/1991 | Garcia-Rill et al. ....................... 607/49 |
| 5,031,618 | 7/1991 | Mullett . |
| 5,058,584 | 10/1991 | Bourgeois . |
| 5,081,990 | 1/1992 | Deletis . |
| 5,119,832 | 6/1992 | Xavier . |

(List continued on next page.)

FOREIGN PATENT DOCUMENTS

| | | |
|---|---|---|
| 19509609 | 10/1995 | Germany . |
| WO 8501213 | 3/1985 | WIPO . |
| WO 9101756 | 2/1991 | WIPO . |
| WO 9207605 | 5/1992 | WIPO . |
| WO 94/01166 | 1/1994 | WIPO . |
| WO 9739797 | 4/1997 | WIPO . |

OTHER PUBLICATIONS van Horne et al., "Multichannel Semiconductor–Based Electrodes for In Vivo Electrochemical and Electrophysiological Studies in Rat CNS", *Neuroscience Letters*, 120, pp 249–252 (1990).

Cooper et al., "The Effect of Chronic Stimulation of Cerebellar Cortex on Epilepsy in Man," *The Cerebellum, Epilepsy, and Behavior*. Cooper Riklan and Snider ed. Plenum Press. NY. pp. 119–171 (1974).

Godsey et al. "Omnitrode: A Simple Cannula for Chemical and Bipolar Electrical Stimulation", *Physiology and Behavior*, Vo. 8, pp. 773–775, Brain Research Publications Inc. 1972 (Great Britain).

Limousin et al., "Effect on Parkinsonian Signs and Symptoms of Biateral Subthalamic Nucleus Stimulation", *The Lancet*, vol. 345, pp. 91–95 (1995).

Benabid, et al., "Chronic Electrical Stimulation of the Ventralis Intermedius Nucleus of the Thalamus as a Treatment of Movement Disorders", *J. Neurosurg*, vol. 84, 203–214 (1996).

Bobo et al., "Convection–enhanced delivery of macromolecules in the brain", *Proc. Natl. Acad. Sci. USA*, vol. 91, pp. 2076–2080 (1994).

Dill, et al., "Dyskinesias in Rats Following Chemical Stimulation of the Neostriatum", *Texas Reports on Biology and Medicine*, vol. 26, No. 1, Spring, pp. 101–106 (1968).

(List continued on next page.)

*Primary Examiner*—William E. Kamm
*Assistant Examiner*—Carl H. Layno
*Attorney, Agent, or Firm*—Banner & Witcoff, Ltd.

[57] ABSTRACT

Techniques using one or more drugs and electrical stimulation for treating neural disorders, including movement disorders resulting in abnormal motor response, by means of an implantable signal generator and electrode and an implantable pump and catheter. A sensor is used to detect activity resulting from the neural disorder. A microprocessor algorithm analyzes the output from the sensor in order to regulate the stimulation and drug dosage delivered to the neural tissue.

56 Claims, 16 Drawing Sheets

U.S. PATENT DOCUMENTS

| | | |
|---|---|---|
| 5,293,879 | 3/1994 | Vonk et al. . |
| 5,423,877 | 6/1995 | Mackey . |
| 5,458,631 | 10/1995 | Xavier ............... 607/117 |
| 5,527,344 | 6/1996 | Arzbaecher et al. ............ 607/3 |
| 5,662,689 | 9/1997 | Elsberry . |
| 5,683,422 | 11/1997 | Rise . |
| 5,697,975 | 12/1997 | Howard, III et al. ............. 607/55 |
| 5,707,396 | 1/1998 | Benabid . |
| 5,711,316 | 1/1998 | Elsberry et al. . |
| 5,713,847 | 2/1998 | Howard et al. . |
| 5,713,923 | 2/1998 | Ward et al. ............... 607/3 |
| 5,716,377 | 2/1998 | Rise et al. . |
| 5,735,814 | 4/1998 | Elsberry et al. . |
| 5,782,798 | 7/1998 | Rise . |
| 5,792,186 | 8/1998 | Rise . |
| 5,800,474 | 9/1998 | Benabid et al. . |
| 5,814,014 | 9/1998 | Elsberry et al. . |
| 5,832,932 | 11/1998 | Elsberry et al. . |
| 5,833,709 | 11/1998 | Rise et al. . |

OTHER PUBLICATIONS

Kroll, et al., "Increasing Volume of Distribution to the Brain with Interstitial Infusion: Dose, Rather Than Convection, Might Be the Most Important Factor", *Neurosurgery*, vol. 38, No. 4, pp. 746–754 (1996).

Graham, et al., Injection of Excitatory Amino Acid Antagonists Into the Medial Pallidal Segment of a 1–Methyl–4–Phenyl–1,2,3,6–tetrahydropyridine (MPTP) Treated Primate Reverses Motor Symptoms of Parkinsonism, *Life Sciences*, vol. 47, pp. PL–91–PL–97 (1990).

Crossman, et al., "Experimental Hemiballismus in the Baboon Produced by Injection of a Gamma–Aminobutryric Acid Antagonist into the Basal Ganglia", *Neuroscience Letters*, 20, pp. 369–372 (1980).

Duncan et al., "Thalamic VPM Nucleus in the Behaving Mondey. III. Effects of Reversible Inactivation by Lidocaine on Thermal and Mechanical Discrimination", *Journal of Neurophysiology*, vol. 70, No. 5 pp. 2086–2096 (1993).

Szerb, "Glutamate release and spreading depression in the facia dentata in response to microdialysis with high $K^{+:\ role\ of\ glia}$", *Brain Research*, 542, pp. 259–265 (1991).

May et al., "Intrastriatal Infusion of Lisuride—A Potential Treatment for Parkinson's Disease? Behavioral and Autoradiographic Studies in 6–OHDA Lesioned Rats", *Neurodegeneration*, vol. 3, pp. 305–313 (1994).

Fig. 13
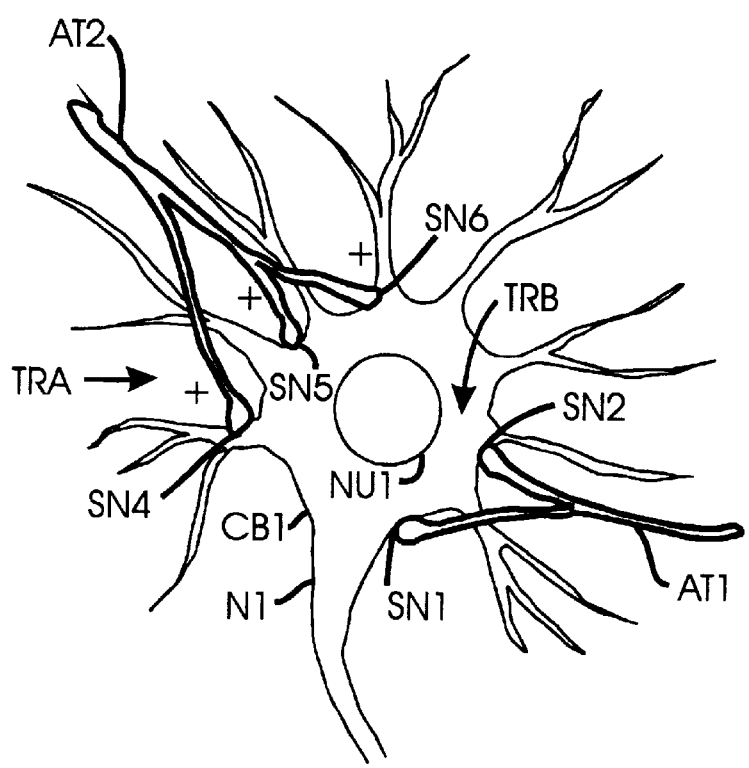
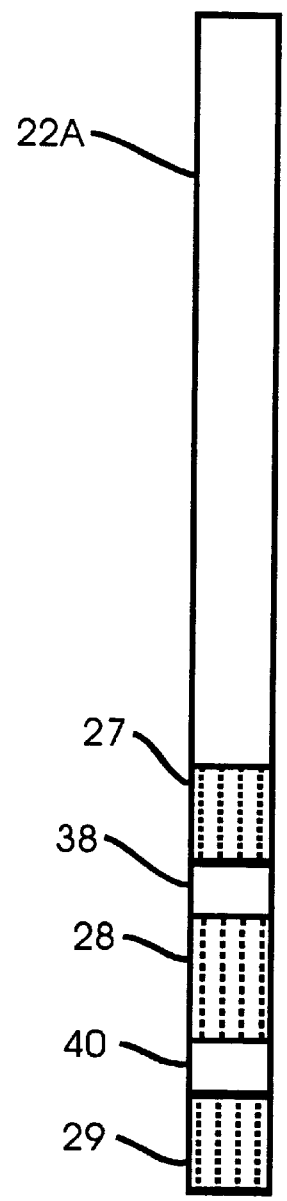

METHOD OF TREATING MOVEMENT DISORDERS BY BRAIN STIMULATION AND DRUG INFUSION

BACKGROUND OF THE INVENTION

1. Field of the Invention

This invention relates to neural tissue stimulation and infusion techniques, and more particularly relates to such techniques for treating various disorders, including movement disorders.

2. Description of Related Art

Patients with neurodegenerative diseases or trauma like cerebral infarct or spinal cord injury can have a variety of movement and muscle control problems, like resting, postural, intention or action tremor; dystonia (improper muscle tone); spasticity (undesirable movements, or muscle co-contraction); dyskinesia (poorly executed movements) or involuntary movements like ballismus, choreiform movements and torticollis (inappropriate movements or limb control). Many of these problems can be called hyperkinesia. Although they can be chronic, or worse, progressive, they also may have times of relative remission. Such problems are found, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia also may result from long term usage of levodopa or other drugs, especially for Parkinson's patients.

Spasticity is defined as a state of excessive muscular tonus (hypertonus) and increased spinal reflexes. This condition exists when the corticospinal pathways have been disrupted. Disruption can occur as a result of stroke causing injury to the fibers as they pass through the internal capsule, a degenerative disorder or physical trauma to the cortex or spinal cord. Loss of this pathway leads to a lack of inhibition of the lower motorneurons which then are more active and responsive to reflexes. In some cases injury to the premotor cortex disrupts the output of the primary motor cortex leading to the similar phenomena.

One form of the Dyskinesia is known as Ballism which typically results in violent flinging movements of the limbs. The movements often affect only one side of the body, in which case the disorder is known as Hemiballism.

In patients suffering essential tremor or tremor due to Parkinson's Disease, the predominant symptom of the disordered movement is tremor. Tremor is often subdivided on the basis of whether the trembling of the limb occurs when the limb is at rest or when muscular contraction is occurring.

Besides being caused by degenerative illness or head injury, tremor can be of unknown origin. One syndrome of idopathic tremor is referred to as essential tremor.

Patients with neurodegenerative diseases or trauma to the basal ganglia like cerebral infarct can have a variety of movement and muscle control problems, like akinesia (impairment in movement initiation), rigidity (stiffness, inflexibility, immobility) or bradykinesia (reduction in amplitude and velocity of movement). These motor disorders may be classified as hypokinetic problems, reflecting an abnormal reduction in voluntary movement. These problems can be chronic, or worse, progressive, but they also may have times of relative remission, especially when drugs are effective. Such problems are common, at certain stages, for patients with Parkinson's disease multiple sclerosis, cerebral palsy, secondary to deafferentation pain, post stroke, post apoplexy or anoxia, post head or spinal trauma, post poisoning, cerebellar disease, etc. Dyskinesia is often a side-effect from medications used for certain symptoms (like tremor, akinesia, rigidity), especially levodopa.

Neurosurgeons have been able to diminish the symptoms of the foregoing movement disorders by lesioning certain brain areas. In addition, it has been demonstrated that open-loop Deep Brain Stimulation (DBS) at high frequencies (100 Hz. or higher) of certain brain structures can alleviate, diminish, or completely stop symptoms of tremor, rigidity, akinesia or hemiballism. Published targets of stimulation include the VIM (ventral intermediate thalamus), subthalamic nucleus, and internal globus pallidus.

It is believed that many symptoms of the foregoing motion disorders are due to dysfunction of the basal ganglia or thalamus. The dysfunction can result in overactivity of the output neurons of the ganglia creating excessive inhibition of the thalamus or underactivity of the ganglia resulting in too little inhibition of the thalamus. If there is too little output activity from the basal ganglia or too little inhibition of the thalamus, a condition such as Ballism or Dystonia will result. If there is too much output activity from the basal ganglia (too much inhibition), a condition such as Hypokinesia will result.

SUMMARY OF THE INVENTION

A preferred form of the invention uses one or more drugs and electrical stimulation to treat a neural disorder. The treatment is carried out by an implantable pump and a catheter having a proximal end coupled to the pump and having a discharge portion for infusing therapeutic dosages of the one or more drugs into a predetermined infusion site in neural tissue. The treatment also is carried out by an implantable signal generator and an implantable electrode having a proximal end coupled to the signal generator and having a stimulation portion for electrically stimulating a predetermined stimulation site in the neural tissue.

By using the foregoing techniques, the symptoms of hypokinetic disorders, such as Parkinson's disease, Akinesia, Bradykinesia or Rigidity, and hyperkinetic disorders, such as Ballism, Hemiballism, Chorea, Torticollis, Spasticity or Dystonia can be alleviated. According to one embodiment of the invention, the stimulation and infusion can decrease excitement of the thalamus or increase inhibition of the thalamus. According to another embodiment of the invention, the stimulation and infusion can increase excitement of the thalamus or decrease inhibition of the thalamus.

Another form of the invention uses a sensor in combination with the signal generator, stimulating electrode, pump and catheter to treat a neural disorder. In this form of the invention, the sensor generates a sensor signal related to activity resulting from said neural disorder. Control means responsive to the sensor signal regulate the signal generator and pump so that the neural disorder is treated.

By using the foregoing techniques, the symptoms of many neural disorders can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 12–17 are diagrammatical views of the catheter-electrode shown in FIG. 1 arranged adjacent various types of neural tissue.

DESCRIPTION OF THE PREFERRED EMBODIMENTS

Figure 1:
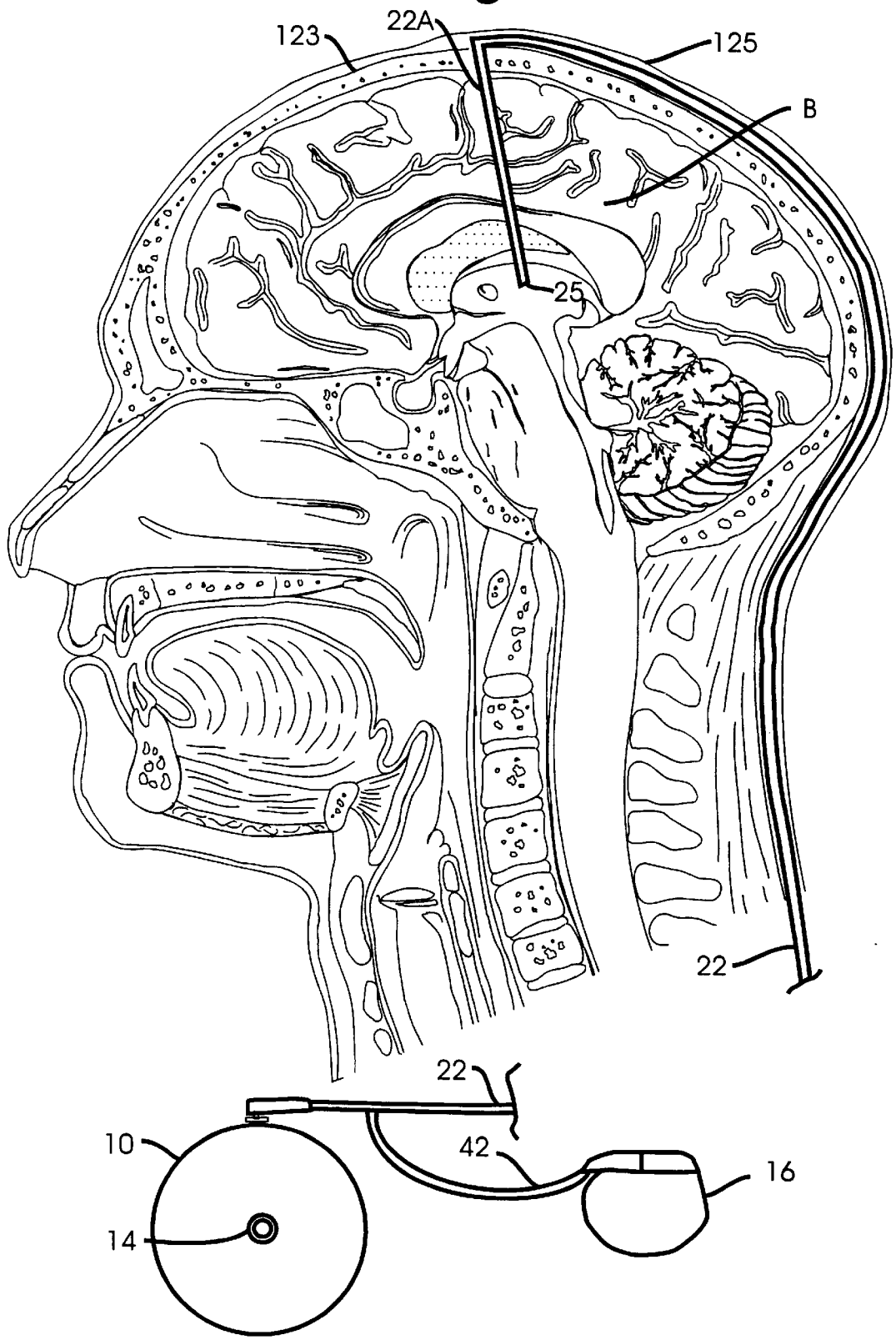
FIG. 1 is a diagrammatic illustration of a combined catheter and electrode implanted in a brain according to a preferred embodiment of the present invention, and a signal generator and pump coupled to the combined catheter and electrode.

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., which is incorporated by reference.

Figure 11:
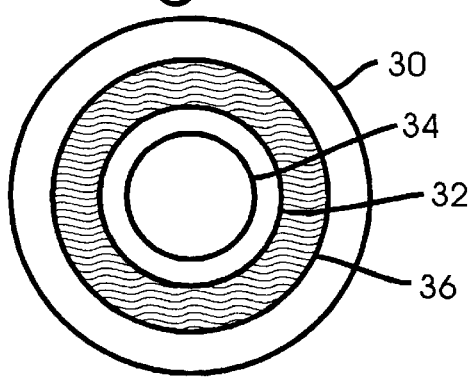
FIG. 11 is a cross sectional view of the catheter-electrode taken along line 11—11 of FIG. 12.

The distal end of catheter 22 terminates in a cylindrical hollow tube 22A having a distal end 25 implanted into a portion of the basal ganglia of the brain by conventional stereotactic surgical techniques. End 25 is provided with microporous portions 27–29 in the preferred embodiment (FIG. 12); however, multiple holes or slits within portions 27–29 could also be used. Additional details about portions 27–29 may be obtained from pending U.S. application Ser. No. 08/430,960 entitled "Intraparenchymal Infusion Catheter System," filed Apr. 28, 1995, in the name of Dennis Elsberry et al. and assigned to the same assignee as the present application. Referring to FIG. 11, tube 22A includes an outer cylindrical insulating jacket 30 and an inner cylindrical insulating jacket 32 that defines a cylindrical catheter lumen 34. A multifilar coil or strands of wire 36 is embedded in tube 22A as shown.

Tube 22A is surgically implanted through a hole in the skull 123 and catheter 22 is implanted between the skull and the scalp 125 as shown in FIG. 1. A stylet may be placed into the center of tube 22A to give it stiffness when introducing the tube into the brain or other neural tissue. After the stylet is removed, center lumen 34 constitutes a catheter which can be used to infuse an agent, including a drug. Catheter 22 is joined to implanted device 10 in the manner shown.

Figure 2:
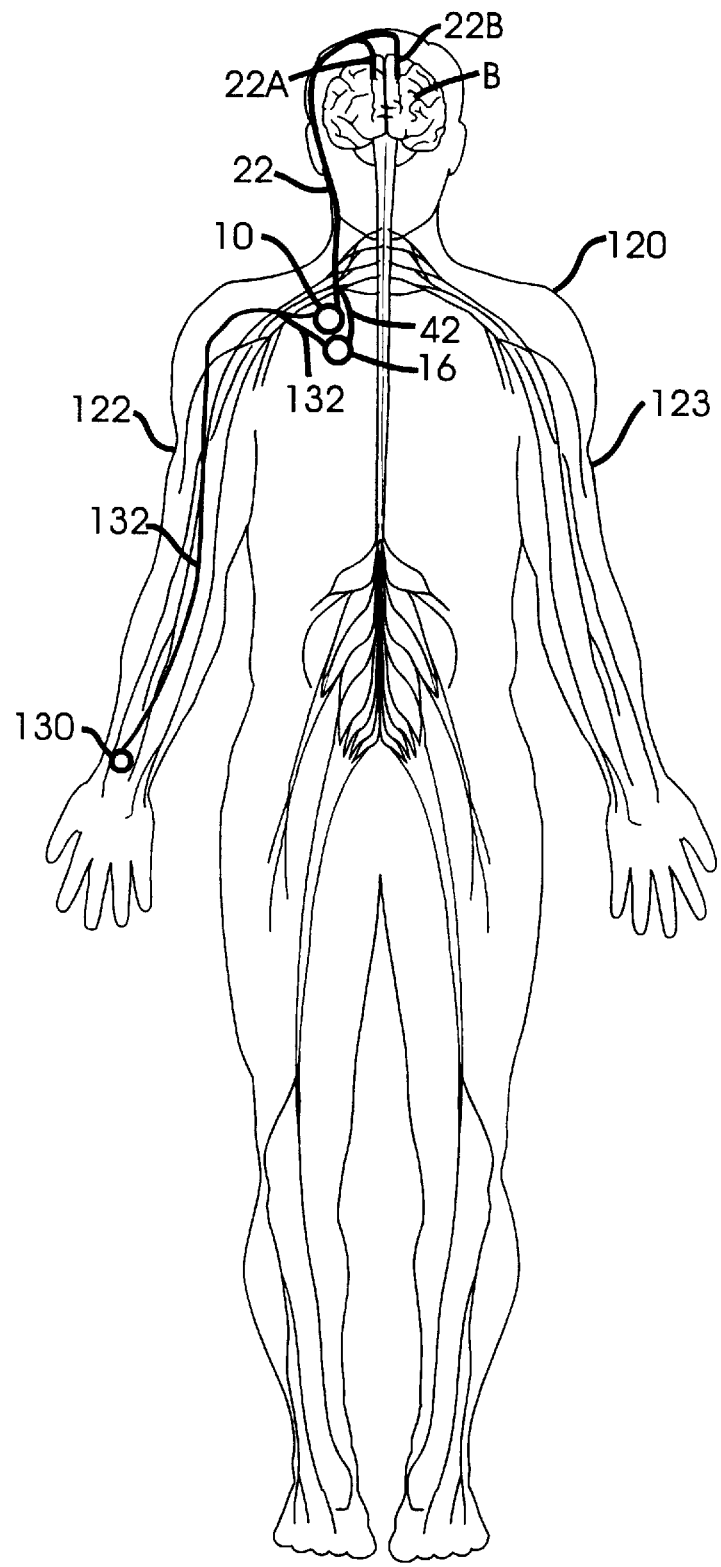
FIG. 2 is a diagrammatic illustration of a portion of the nervous system of the human body in which a preferred form of motion sensor, signal generator, pump and combined catheter and electrode have been implanted.

Referring to FIG. 2, device 10 is implanted in a human body 120 in the location shown. Body 120 includes arms 122 and 123. Alternatively, device 10 may be implanted in the abdomen.

Catheter 22 may be divided into twin tubes 22A and 22B that are implanted into the brain bilaterally as shown. Alternatively, tube 22B may be supplied with drugs from a separate catheter and pump.

Referring again to FIG. 1, a system or device 16 made in accordance with the preferred embodiment also may be implanted below the skin of a patient. Device 16 may take the form of a signal generator Model 7424 manufactured by Medtronic, Inc. under the trademark Itrel II which is incorporated by reference.

Figure 12:
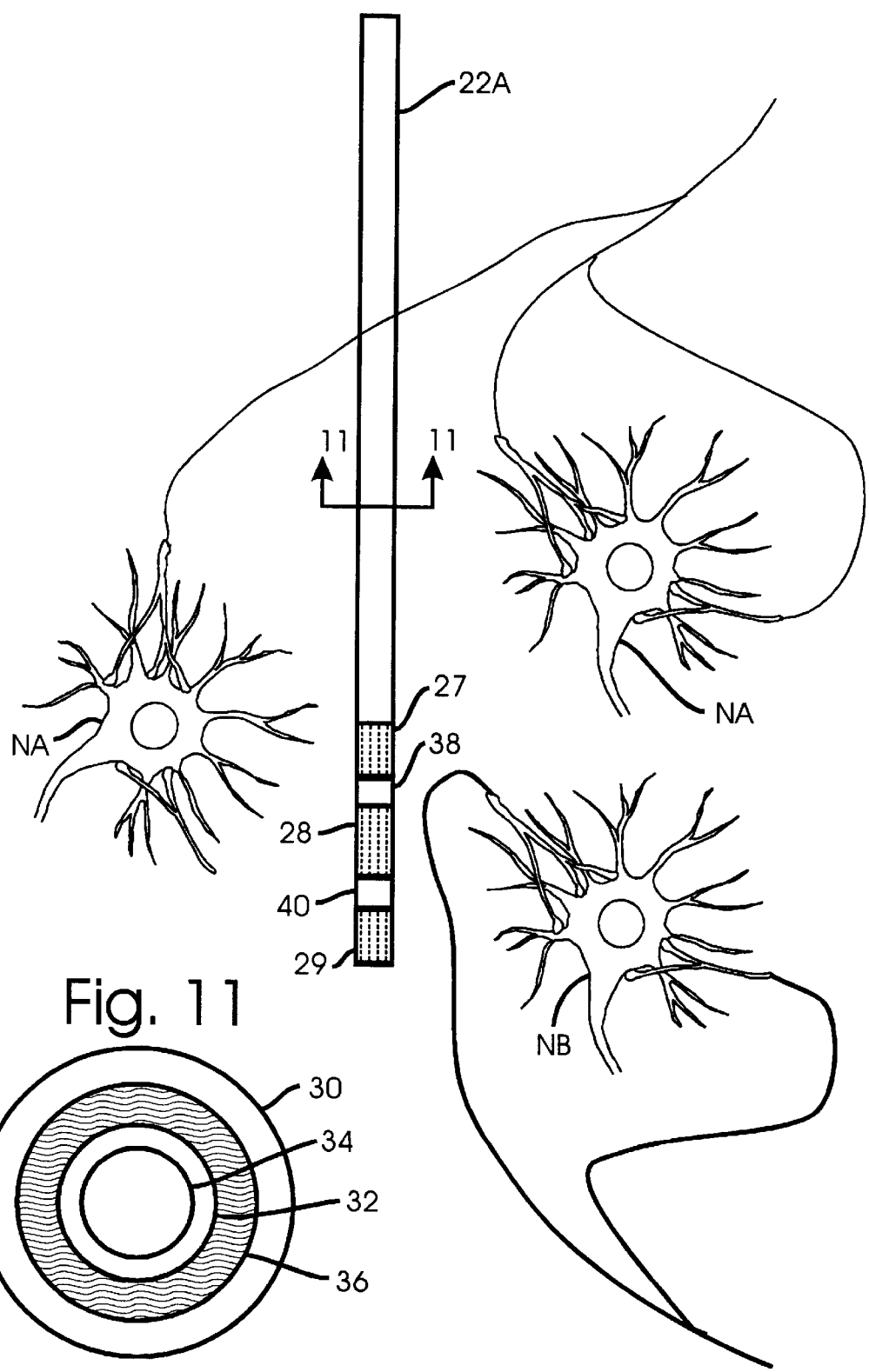

The distal end of tube 22A terminates in stimulation electrodes 38 and 40 (FIG. 12). Each of electrodes 38 and 40 is individually connected to device 16 through a conductor in wire 36 (FIG. 11). The wires exit catheter 22 to form a cable 42 which is joined to implanted device 16 in the manner shown in FIG. 1. While the preferred embodiment shows two electrodes on tube 22A (FIG. 12), some applications may require a greater number.

Referring to FIG. 2, device 16 is implanted in a human body 120 in the location shown. Alternatively, device 16 may be implanted elsewhere, such as in the abdomen.

A sensor 130 is implanted into a portion of a patient's body suitable for detecting symptoms of the motion disorder being treated. Sensor 130 is adapted to sense an attribute of the symptom to be controlled or an important related symptom. For motion disorders that result in abnormal movement of an arm, such as arm 122, sensor 130 may be a motion detector implanted in arm 122 as shown. For example, sensor 130 may sense three-dimensional or two-dimensional motion (linear rotational or joint motion), such as by an accelerometer. One such sensor suitable for use with the present invention is described in U.S. Pat. No. 5,293,879 (Vonk et al.). Another suitable accelerometer is found in pacemakers manufactured by Medtronic, Inc. and described in patent application Ser. No. 08/399072 entitled "Package Integrated Accelerometer", filed Mar. 8, 1995, in the names of James Sikorski and Larry R. Larson. Sensor 130 also may be placed in device 10 in order to detect abnormal movement resulting from the motion disorder being treated.

Sensor 130 also may be capable of detecting gravity direction or motion relative to some object (e.g., a magnet) either implanted or fixed nearby. Sensor 130 also may take the form of a device capable of detecting force in muscles or at joints, or pressure.

Sensor 130 may detect muscle EMG in one, two or more muscles, or in reciprocal muscles at one joint. For such detection, sensor 130 may take the form of a lead with one or more recording electrodes inserted into the muscle of interest.

Brain EEG (e.g., motor cortex potentials recorded above the motor neurons controlling specific muscle groups) also may be detected by sensor 130.

Yet another form of sensor 130 would include a device capable of detecting nerve compound action potentials (e.g., either sensory afferent information from muscle or skin receptors or efferent motor potentials controlling a muscle of interest).

For certain types of patients, sensor 130 may take the form of a device detecting the posture of the patient, such as the device shown in U.S. Pat. No. 5,031,618 (Mullett).

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule, motor cortex or basal ganglia of the brain. Signals that are received by the sensor may by amplified before transmission to circuitry contained within device 10 or device 16.

Sensor 130 may take the form of a transducer consisting of an electrode with an ion selective coating applied which is capable of directly transducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters,* 120 (1990) 249–252.

For tremor, the relative motion of a joint or limb or muscle EMG may be productively sensed. Sensing electrical activity of neurons in various locations of the motor circuitry also is helpful. Recording the electrical activity in the thalamus will reveal a characteristic oscillating electrical activity when tremor is present.

For Ballism, Hemiballism or tremor, sensor 130 may take the form of an accelerometer detecting relative motion of a joint or limb or muscle EMG.

For Dystonia, sensor 130 may take the form of a device for detecting relative motion of a joint or limb or muscle EMG.

Figure 3:
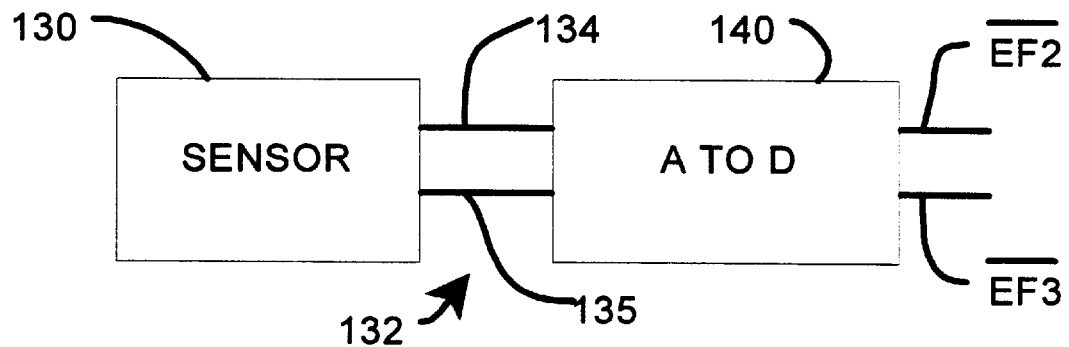
FIG. 3 is a schematic block diagram of a sensor and analog to digital converter circuit used in the preferred embodiment of the invention.

Referring to FIG. 3, the output of sensor 130 is coupled by a cable 132 comprising conductors 134 and 135 to the input of analog to digital converter 140. Alternatively, the output of an external feedback sensor would communicate with the implanted pulse generator through a telemetry downlink. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A would be disconnected.

The present invention may be implemented by providing seven different drug dosages from 0 dosage to a 1.0 ml dosage with 0.1 ml increments between choices. The time interval between dosages can be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B) of the '147 Patent. The appropriate drug dosage and interval is selected by a computer algorithm that reads the output of converter 140 and makes the appropriate selection.

Figure 4:
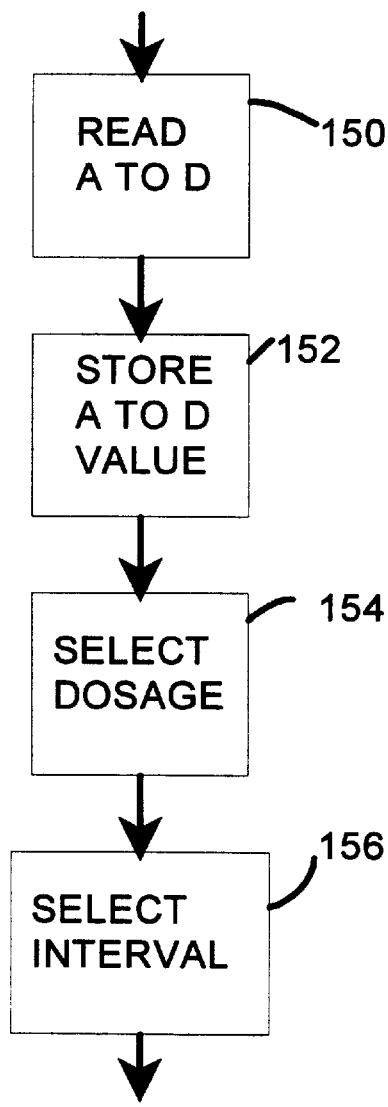
FIG. 4 is a flow chart illustrating a preferred form of a microprocessor program for utilizing the sensor to control drug dosage administered to the brain.

One exemplary computer algorithm is shown in FIG. 4. Microprocessor 100 included within device 10 reads converter 140 in step 150, and stores one or more values in RAM 102a in step 152. One of seven dosages is selected in step 154, and an appropriate time interval is selected in step 156. The selected dosage and interval of a drug is then delivered through catheter 22 and tube 22A to the basal ganglia of the brain as described in the '147 Patent.

For some types of motion disorders, a microprocessor and analog to digital converter will not be necessary. The output from sensor 130 can be filtered by an appropriate electronic filter in order to provide a control signal for a pump of the type shown in the '147 Patent.

The type of drugs administered by device 10 into the brain depend on the specific location at which distal end 25 of tube 22A is surgically implanted. The appropriate drugs for use in connection with the portion of the basal ganglia or thalamus in which tube 22A terminates, together with the effect of the drug on that portion of the brain for hyperkinetic motion disorders is provided in the following Table I:

TABLE I

| EFFECT | PORTION OF BRAIN | DRUG |
| --- | --- | --- |
| DECREASE EXCITATION INCREASE | VL THALAMUS | GLUTAMATE ANTAGONIST/ DEGRADING ENZYME |
| INCREASE INHIBITION | VL THALAMUS | GABA AGONIST/ REUPTAKE BLOCKER |
| INCREASE EXCITATION | GPi/SNr | GLUTAMATE AGONIST/ REUPTAKE BLOCKER |
| DECREASE INHIBITION | GPi/SNr | GABA ANTAGONIST/ DEGRADING ENZYME |
| INCREASE EXCITATION | STN | GLUTAMATE AGONIST/ REUPTAKE BLOCKER |
| DECREASE INHIBITION | STN | GABA ANTAGONIST/ DEGRADING ENZYME |
| DECREASE EXCITATION | GPe | GLUTAMATE ANTAGONIST/ DEGRADING ENZYME |
| INCREASE INHIBITION | GPe | GABA AGONIST/ REUPTAKE BLOCKER |
| INCREASE EXCITATION | Neostriatum (Indirect pathway) | GLUTAMATE AGONIST/ REUPTAKE BLOCKER |
| DECREASE INHIBITION | Neostriatum (Indirect pathway) | DOPAMINE ANTAGONIST/ DEGRADING ENZYME |
| DECREASE EXCITATION | Neostriatum (Direct pathway) | GLUTAMATE ANTAGONIST/ DEGRADING ENZYME |
| DECREASE EXCITATION | Neostriatum (Direct pathway) | DOPAMINE ANTAGONIST/ DEGRADING ENZYME |
| INCREASE EXCITATION | Motor Cortex | GLUTAMATE AGONIST |

The appropriate drugs for use in connection with the portion of the basal ganglia or thalamus in which tube 22A terminates, together with the effect of the drug on that portion of the brain for hypokinetic motion disorders is provided in the following Table II:

TABLE II

| EFFECT | PORTION OF BRAIN | DRUG |
| --- | --- | --- |
| INCREASE EXCITATION | VL THALAMUS | Glutamate agonist |
| DECREASE INHIBITION | VL THALAMUS | GABA antagonist |
| INCREASE INHIBITION | GPi/SNr | GABA agonist |
| DECREASE EXCITATION | GPi/SNr | Glutamate antagonist |
| INCREASE INHIBITION | STN | GABA agonist |
| DECREASE EXCITATION | STN | Glutamate antagonist |
| INCREASE EXCITATION | GPe | Glutamate agonist |
| DECREASE INHIBITION | GPe | GABA antagonist |
| INCREASE DOPAMINE | STRIATUM | Dopamine agonist |

In the foregoing Tables I and II, VL Thalamus means ventrolateral thalamus; GPi means internal segment of globus pallidus; SNr means substantia nigra pars reticulata, STN means subthalamic nucleus; neostriatum means the combination of the caudate nucleus and the putamen; and GPe means external segment of globus pallidus.

Typical stereotaxic coordinates for the portions of a normal brain described in Tables I and II are identified in the following Table III:

TABLE III

| BRAIN REGION | MEDIAL-LATERAL DIMENSION | DORSAL-LATERAL DIMENSION | ANTERIOR-POSTERIOR DIMENSION |
|---|---|---|---|
| VL Thalamus | 0.7 to 1.8 | 1.5 to −0.2 | 0.0 to −1.0 |
| Gpi | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to; all dimensions are in centimeters.

Exemplary ranges of dosages and drug concentrations for the drugs identified in Tables I and II are provided in the following Table IV:

In the preceding table, muM means micromolar.

A drug can be delivered essentially continuously (within the constraints of the particular delivery device being used) or it may be delivered during intermittent intervals coordinated to reflect the half-life of the particular agent being infused or circadian rhythms. As an example, the motor symptoms may normally subside at night when the person is sleeping so the drug delivery rates might be reduced to coincide with the hours between 10 p.m. and 7 a.m.

Microprocessor 100 within device 10 can be programmed so that a controlled amount of drug can be delivered to the specific brain sites described in Table I. Alternatively, sensor 130 can be used with a closed loop feedback system in order to automatically determine the level of drug delivery necessary to alleviate motor disorder symptoms as described in connection with FIG. 4.

Figure 5:
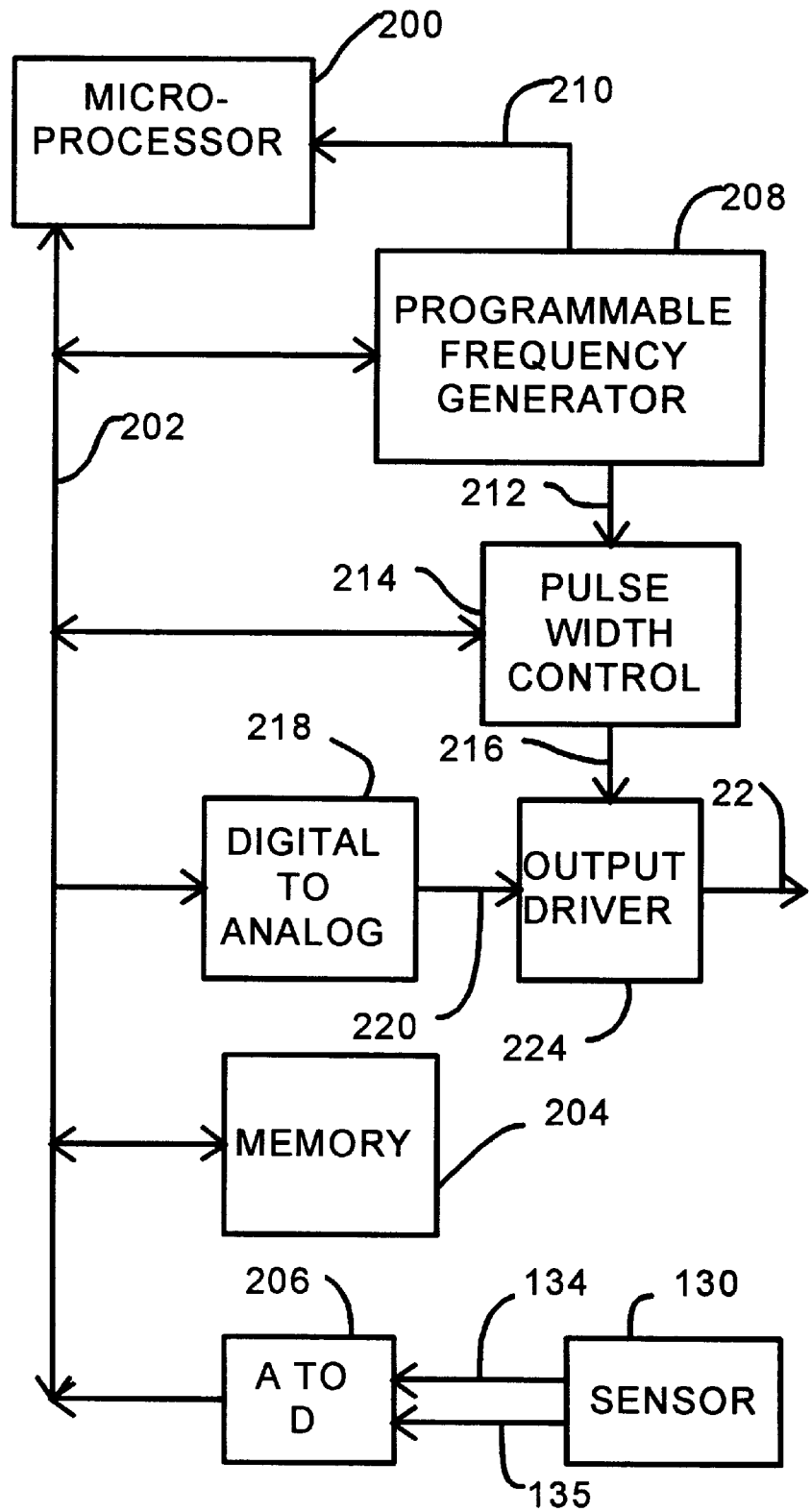
FIG. 5 is a schematic block diagram of a microprocessor and related circuitry for utilizing the sensor to control stimulation administered to the brain.

The applicants have discovered that the efficacy of treatment may be enhanced if the neural tissue is stimulated while drugs are being administered as described above. The stimulation can be achieved by a modified form of the ITREL II signal generator implemented as device 16 (FIG. 1) which is described in FIG. 5. The output of sensor 130 is coupled by cable 132, comprising conductors 134 and 135, to the input of an analog to digital converter 206. Alternatively, the output of an external sensor would communicate with the implanted pulse generator through a telemetry downlink. The output of the analog to digital converter 206 is connected to a microprocessor 200 through a peripheral bus 202 including address, data and control lines. Microprocessor 200 processes the sensor data in different ways depending on the type of transducer in use.

TABLE IV

| DESIRED EFFECT | BRAIN TARGET OR TARGETS | DRUG CLASS | SPECIFIC DRUG | DOSING RANGE |
|---|---|---|---|---|
| Decrease Excitation | Ventrolateral Thalamus | Glutamate Antagonists | MK801 (dizocilpine) ketamine HCL | 1–20 muM 5–50 muM |
| Increase Excitation | Ventrolateral Thalamus | GABA Agonists | baclofen muscinol Hbr | 1–10 muM 100–500 muM |
| Decrease Inhibition | Globus Pallidus Interna/Substantia Nigra reticulata | Glutamate Agonist | D-Cycloserine L-AP4 | 1–10 muM 1–10 muM |
| Increase Excitation | Subthalamic Nucleus | Glutamate Agonist | Carboxyphenylglycine L-glutamic acid | 10–500 muM 1–100 muM |
| Decrease Inhibition | Subthalamic Nucleus | GABA Antagonists | Bicuculline picrotoxin | 1–100 muM 10–100 muM |
| Decrease Excitation | Globus Pallidus Externa | Glutamate Antagonist | AP-3 Dextromethorphan | 1–10 muM 1–100 muM |
| Increase Inhibition | Globus Pallidus Externa | GABA Agonists | baclofen Muscinol Hbr | 0.1–10 muM 100–500 muM |
| Increase Excitation | Striatum (Indirect Pathway) | Glutamate Agonists | cis-Piperidine-2,3-dicarboxylic acid D-Cycloserine | 1–10 muM 1–10 muM |
| Decrease Inhibition | Striatum (Indirect Pathway) | Dopamine Antagonist | (+)apomorphine HCL (−)Sulpiride | 5–20 muM 0.05–1 muM |
| Decrease Excitation | Striatum (Indirect Pathway) | Glutamate Antagonist | MCPD dextrorphan tartrate | 0.02–10 muM 1–100 muM |
| Increase Excitation | Neostriatum | Dopamine Agonist | (−) apomorphine pergolide methanesulfonate | 10–30 muM 1–10 muM |
| Increase Excitation | Motor Cortex | Glutamate Agonists | (+/−) trans-ACPD L-AP4 | 1–10 muM 1–10 muM |

When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 22 and lead 22A to the basal ganglia, thalamus or other region of the brain.

Microprocessor 200 executes an algorithm shown in FIGS. 6–10 in order to provide stimulation with closed loop feedback control. At the time the stimulation device 16 is implanted, the clinician programs certain key parameters into the memory of the implanted device via telemetry. These parameters may be updated subsequently as needed. Step 400 in FIG. 6 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which device 10 may use to optimize the therapy. The clinician may also choose the order in which the parameter changes are made (step 400(6)). Alternatively, the clinician may elect to use default values.

Figure 6:
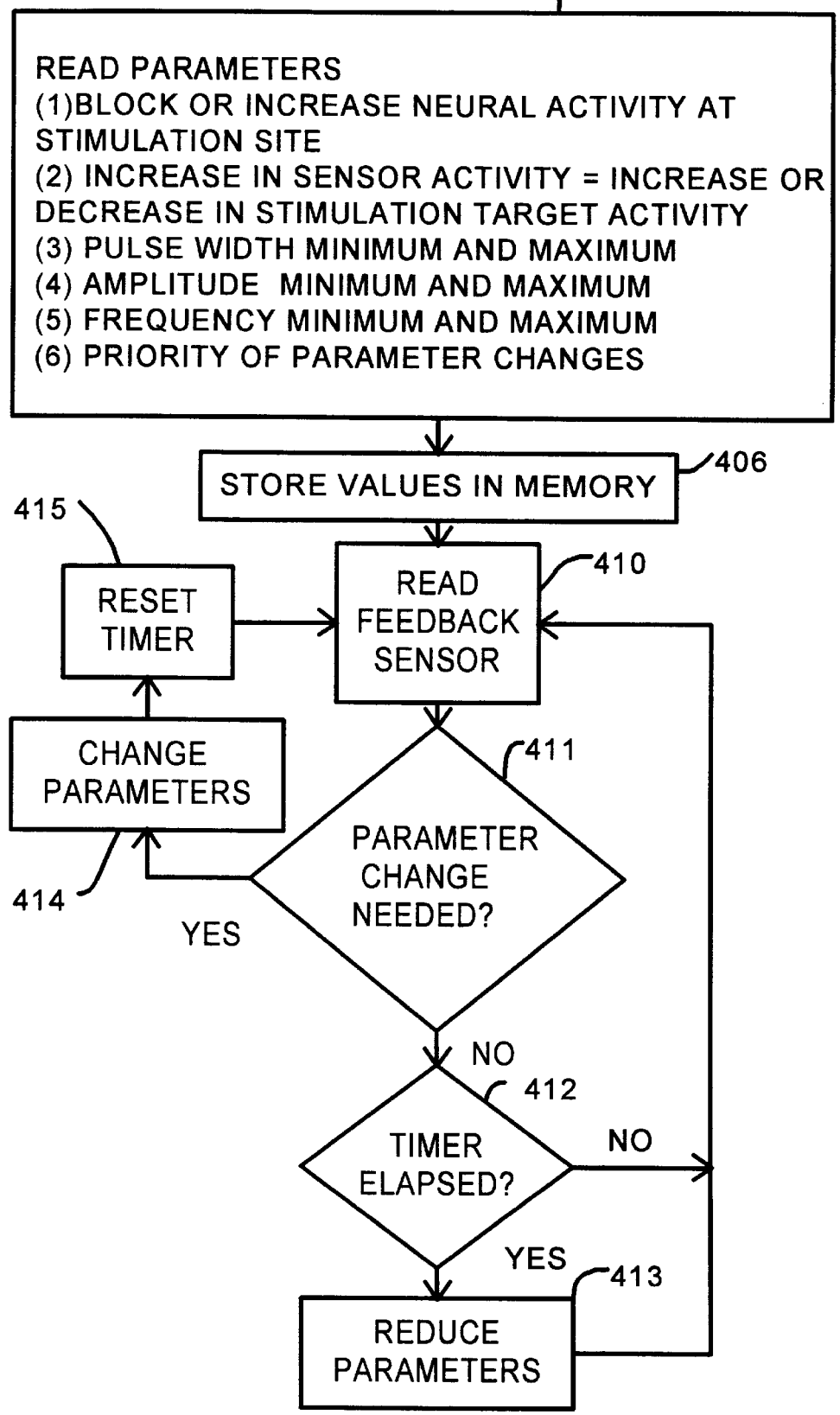
FIGS. 6–10 are flow charts illustrating a preferred form of microprocessor program for generating stimulation pulses to be administered to the brain.

The algorithm for selecting parameters is different depending on whether the clinician has chosen to block the neural activity at the stimulation target or facilitate the neural activity. FIG. 6 details steps of the algorithm to make parameter changes.

Figure 7:
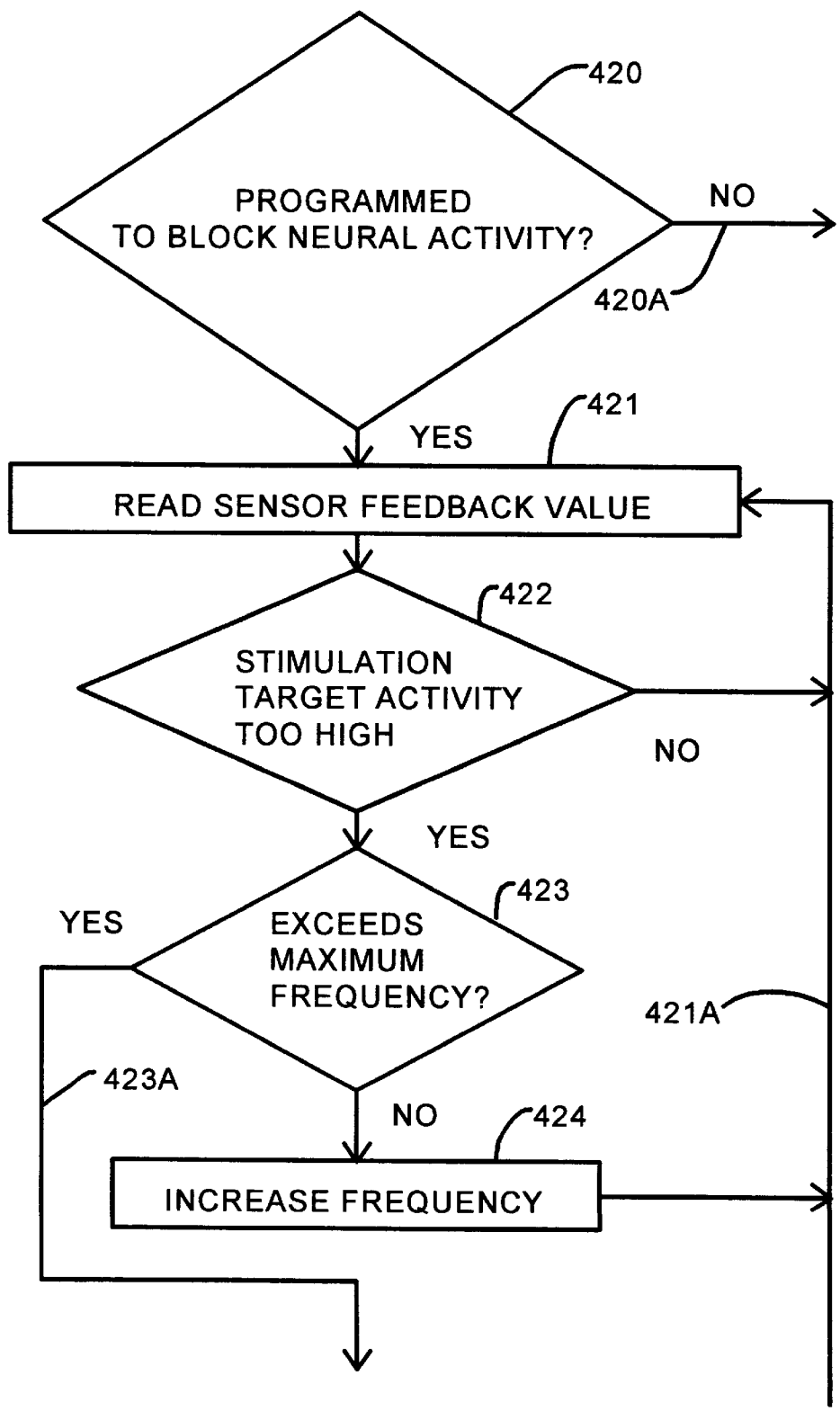
Figure 8:
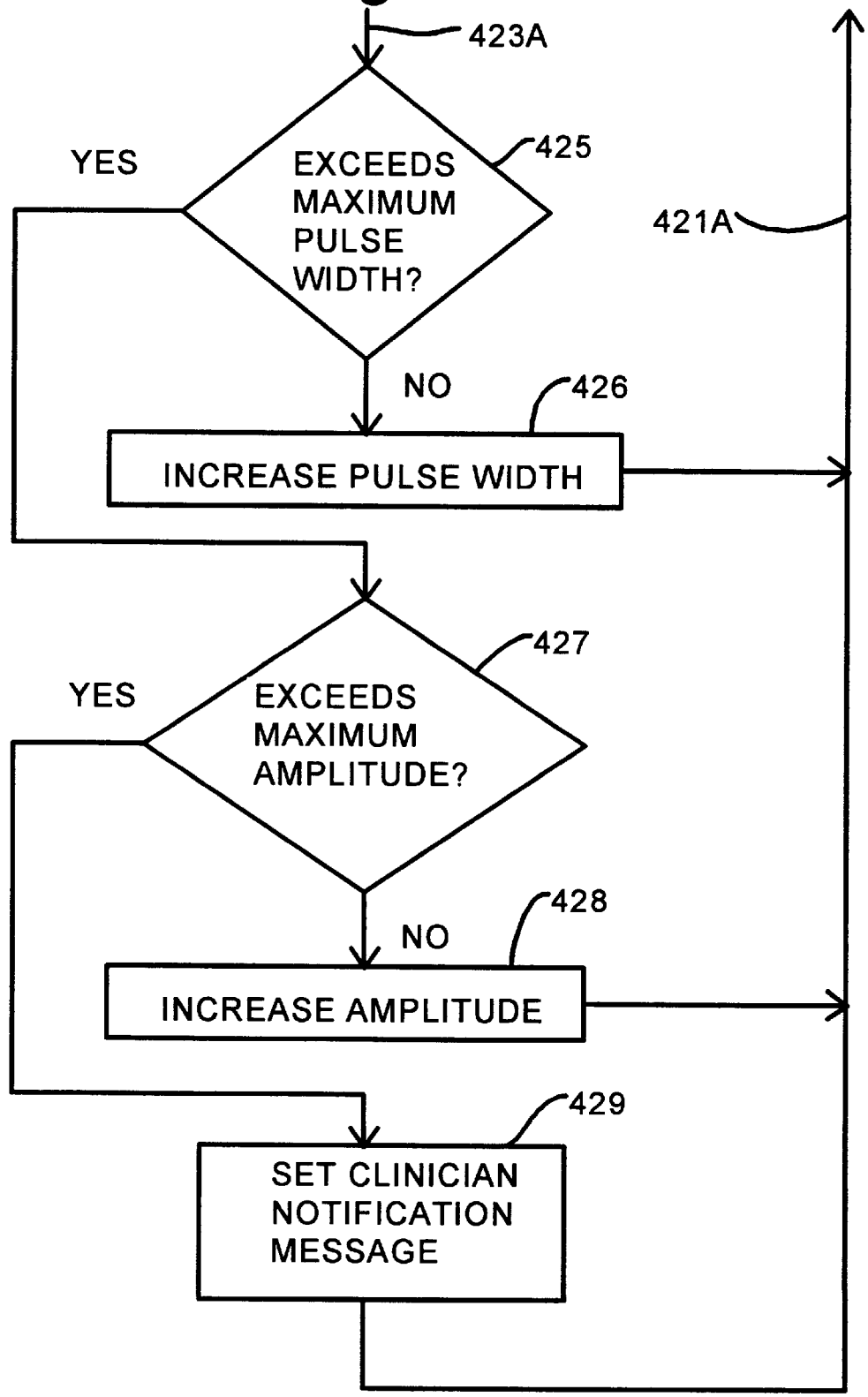
Figure 9:
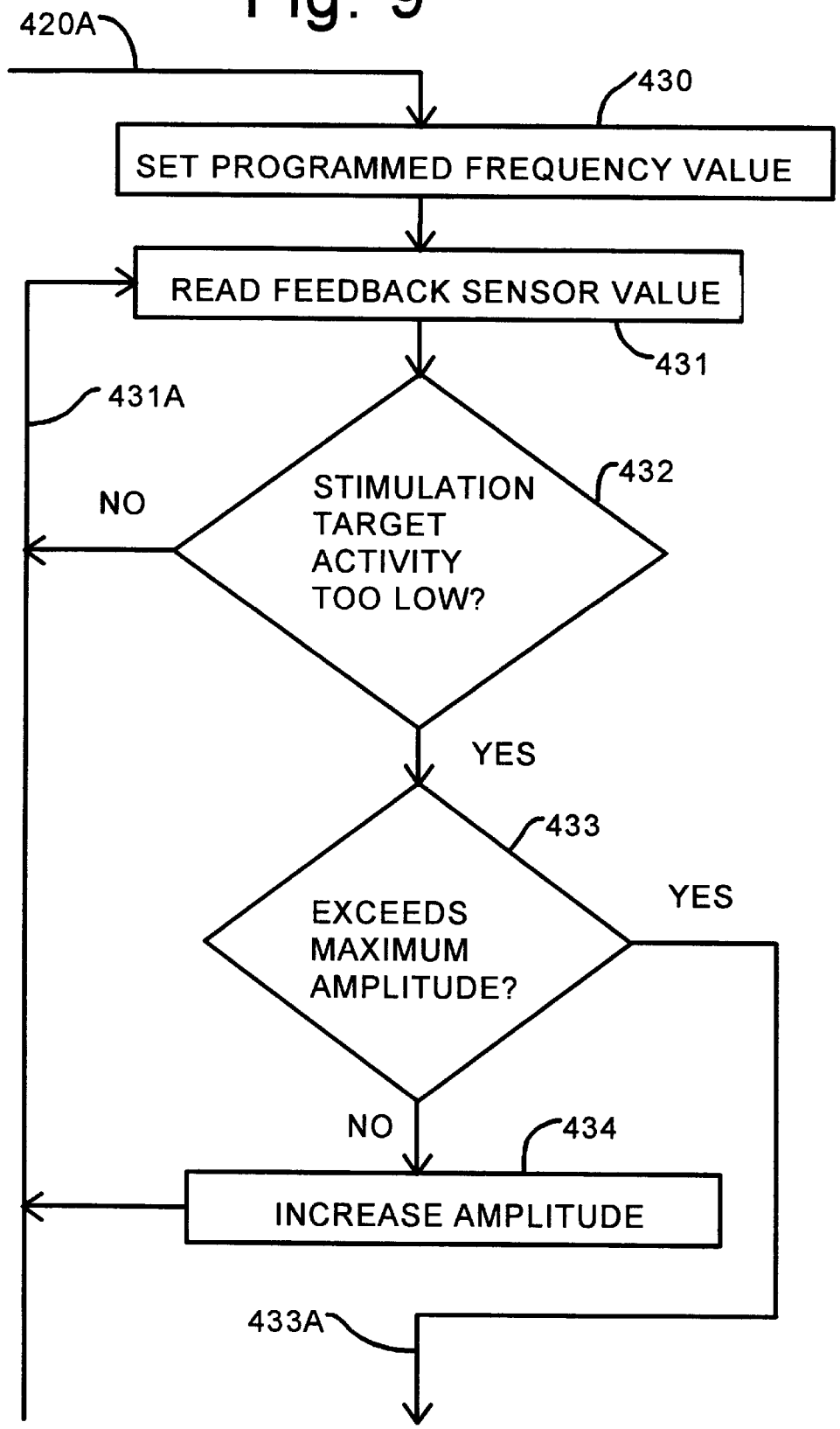

The algorithm uses the clinician programmed indication of whether the neurons at the particular location of the stimulating electrode are to be facilitated or blocked in order to reduce the neural activity in the subthalamic nucleus to decide which path of the parameter selection algorithm to follow (step 420, FIG. 7). If the neuronal activity is to be blocked, device 16 first reads the feedback sensor 130 in step 421. If the sensor values indicate the activity in the glutamatergic neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130. If the frequency parameter is at the maximum, the algorithm next increases the pulse width in step 426 (FIG. 8), again with the restriction that this parameter has not exceeded the maximum value as checked for in step 425 through path 423A.

Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 10:
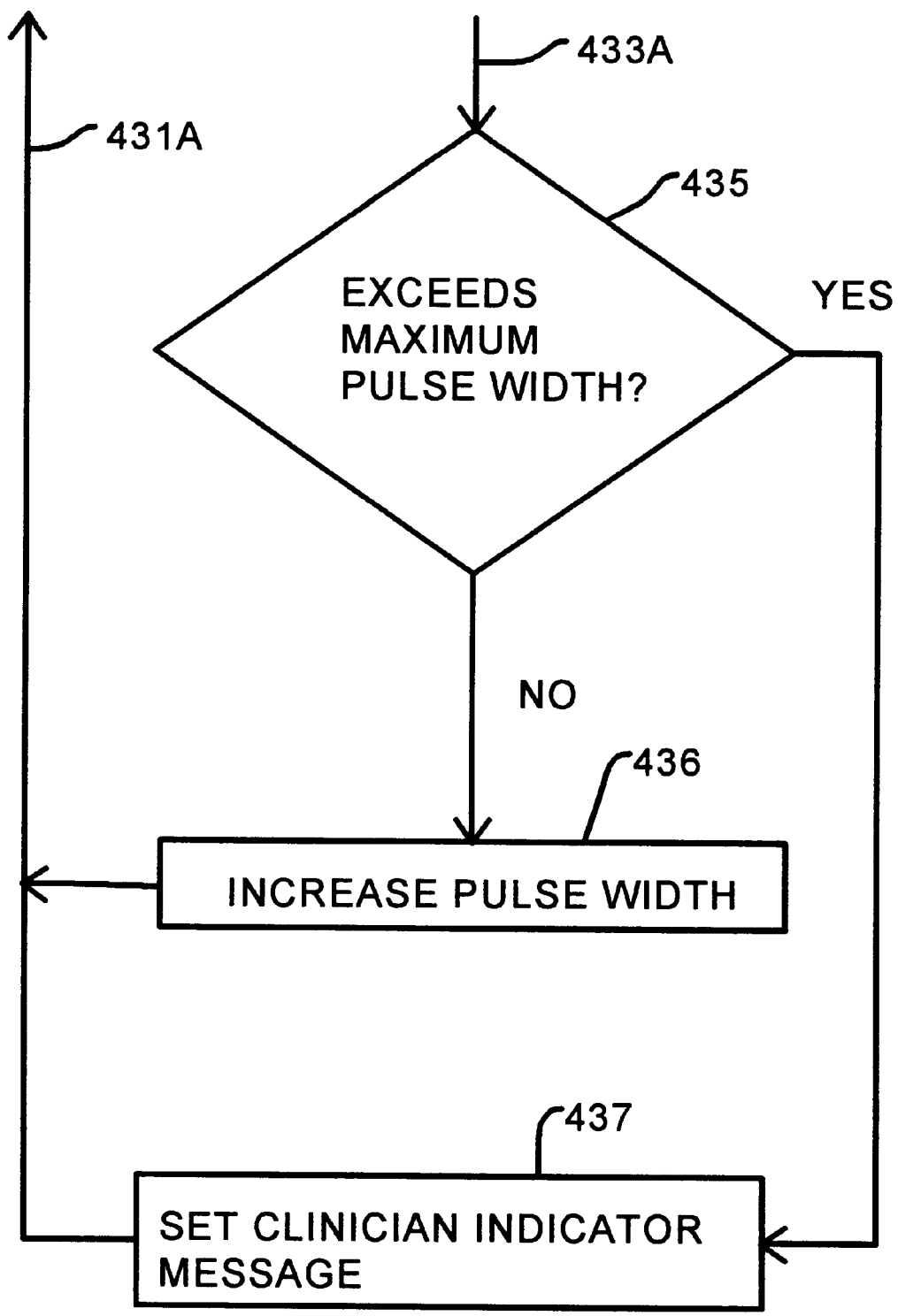

If, on the other hand, the stimulation electrode is placed in a location which the clinician would like to activate in order to increase an inhibition of the subthalamic nucleus, the algorithm would follow a different sequence of events. In the preferred embodiment, the frequency parameter would be fixed at a value chosen by the clinician to facilitate neuronal activity in step 430 (FIG. 9) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 10). A lack of adequate reduction of neuronal activity in the subthalamic nucleus, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in, for example, the subthalamic nucleus. Superimposed on the algorithm just described is an additional algorithm to readjust all the parameter levels downward as far as possible. In FIG. 6, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, device 16 tries reducing a parameter in step 413 to determine if control is maintained. If it is, the various parameter values will be ratcheted down until such time as the sensor values again indicate a need to increase them. While the algorithms in FIG. 6 follow the order of parameter selection indicated, other sequences may be programmed by the clinician.

Electrical stimulation of neural tissue may be implemented by providing pulses to electrodes 38 and 40 (FIG. 12) having amplitudes of 0.1 to 20 volts, pulse widths varying from 0.02 to 1.5 milliseconds, and repetition rates varying from 2 to 2500 Hz. The appropriate stimulation pulses are generated by device 16 based on the computer algorithm illustrated in FIGS. 6–10. Pulses with the selected characteristics are then delivered from device 16 through cable 42, catheter 22, tube 22A and electrodes 38 and 40 to the basal ganglia or thalamus of the brain.

For some types of motion disorders, a microprocessor and analog to digital converter will not be necessary. The output from sensor 130 can be filtered by an appropriate electronic filter in order to provide a control signal for device 16.

The type of stimulation administered by device 16 to the brain depends on the specific location at which the electrodes 38 and 40 of tube 22A are surgically implanted. The appropriate stimulation for the portion of the basal ganglia or thalamus in which tube 22A terminates, together with the effect of the stimulation on that portion of the brain for hyperkinetic motion disorders is provided in the following Table V:

of the caudate nucleus and the putamen; and GPe means external segment of globus pallidus.

Coordinates for the portions of the brain described in Tables IV and V are the same as described in connection with Table III.

TABLE V

| EFFECT | STIMULUS TYPE | LOCATION |
|---|---|---|
| DECREASE EXCITATION OF VL THALAMUS | HIGH FREQ. BLOCKING STIMULATION | VL THALAMUS |
| INCREASE INHIBITION OF VL THALAMUS | LOW FREQ. ACTIVATING STIMULATION | Pallido-thalamic axons (AL and LT) |
| INCREASE EXCITATION OF GPi/SNr | LOW FREQ. ACTIVATING STIMULATION | GPi/SNr |
| INCREASE EXCITATION OF GPi/SNr | LOW FREQ. ACTIVATING STIMULATION | Subthalamic to pallidal fiber tracts |
| DECREASE INHIBITION OF GPi/SNr | HIGH FREQ. BLOCKING STIMULATION | Neostriatum |
| INCREASE EXCITATION OF STN | LOW FREQ. STIMULATION | STN Nucleus |
| DECREASE INHIBITION OF STN | HIGH FREQ. BLOCKING STIMULATION | GPe |
| DECREASE EXCITATION OF VL THALAMUS | HIGH FREQ. BLOCKING STIMULATION | VL THALAMUS |
| DECREASE EXCITATION OF GPe | HIGH FREQ. BLOCKING STIMULATION | GPe |
| INCREASE OF GPe | LOW FREQ. STIMULATION | Neostriatum |
| INCREASE OF GPe | LOW FREQ. STIMULATION | Neostriatum to Gpe fibers (i.e., border of nucleus) |

The appropriate stimulation for use in connection with the portion of the basal ganglia or thalamus in which tube 22A terminates, together with the effect of the stimulation on that portion of the brain for hypokinetic motion disorders is provided in the following Table VI:

A microprocessor or custom integrated circuit within device 16 can be programmed so that the desired stimulation can be delivered to the specific brain sites described in Tables IV and V. Alternatively, sensor 130 can be used with a closed loop feedback system in order to automatically

TABLE VI

| EFFECT | STIMULUS TYPE | LOCATION |
|---|---|---|
| INCREASE EXCITATION OF VL THALAMUS | LOW FREQ. STIMULATION | VL THALAMUS |
| DECREASE INHIBITION OF VL THALAMUS | HIGH FREQ. BLOCKING STIMULATION | GPi/SNr |
| INCREASE INHIBITION OF GPi/SNr | LOW FREQ. STIMULATION | Striatopallidal fiber pathway |
| INCREASE INHIBITION OF GPi/SNr | LOW FREQ. STIMULATION | Neostriatum |
| DECREASE EXCITATION OF GPi/SNr | HIGH FREQ. BLOCKING STIMULATION | GPi/SNr |
| INCREASE INHIBITION OF STN | LOW FREQ. STIMULATION | GPe to STN fiber pathway |
| INCREASE INHIBITION OF STN | LOW FREQ. STIMULATION | GPe |
| DECREASE EXCITATION OF STN | HIGH FREQ. BLOCKING STIMULATION | STN |
| INCREASE EXCITATION OF VL THALAMUS | LOW FREQ. STIMULATION | VL THALAMUS |
| INCREASE EXCITATION OF GPe | LOW FREQ. ACTIVATING STIMULATION | GPe |
| DECREASE INHIBITION OF GPe | HIGH FREQ. BLOCKING STIMULATION | Neostriatum |
| INCREASE INHIBITION OF GPi/SNr | LOW FREQ. ACTIVATING STIMULATION | STRIATOPALLIDAL FIBER PATHWAYS |

In the foregoing Tables V and VI, VL Thalamus means ventrolateral thalamus; GPi means internal segment of globus pallidus; SNr means substantia nigra pars reticulata, STN means subthalamic nucleus; LT means the Lenticulo-thalamic fiber pathway; neostriatum means the combination determine the type of stimulation necessary to alleviate motor disorder symptoms as described in connection with FIGS. 5–10.

The foregoing techniques for simultaneous drug infusion and electrical stimulation can be applied to neural tissue in general, and is not limited to the previously described locations in the brain. FIG. 12 describes one such application in which type A neurons, such as NA, are located in the same region as type B neurons, such as NB. By infusing various agents through portions 27–29, neurons NA can be inhibited or excited with respect to their response to electrical stimulation provided by electrodes 38 and 40, while neurons NB remain unchanged with respect to their response to such stimulation. Thus, neurons NA or NB can be selectively stimulated by electrodes 38 and 40 due to the infusion of substances through portions 27–29 of tube 22A.

Referring to FIG. 13, a neuron N1 has a cell body CB1 and a nucleus NU1. Neuron N1 can be excited by axon terminals AT1 at synapses SN1–SN2 by an inhibitory neurotransmitter TRB and can be excited by axon terminals AT2 at synapses SN4–SN6 by an excitatory neurotransmitter TRA. Portions 27–29 are used to infuse into the region of neuron N1 one or more of the following agents: an antagonist of transmitter TRB, an agonist of transmitter TRA, an agent to block the reuptake of transmitter TRA, a degradative enzyme for transmitter TRB and potassium. The agents can be infused separately or together in a cocktail. Such infusion leads to partial depolarization of neuron N1 and to a reduced threshold to stimulation by electrodes 38 and 40. That is, after infusion, the amplitude of stimulation required to create action potentials in neuron N1 is reduced compared to the time period before infusion.

Figure 14:
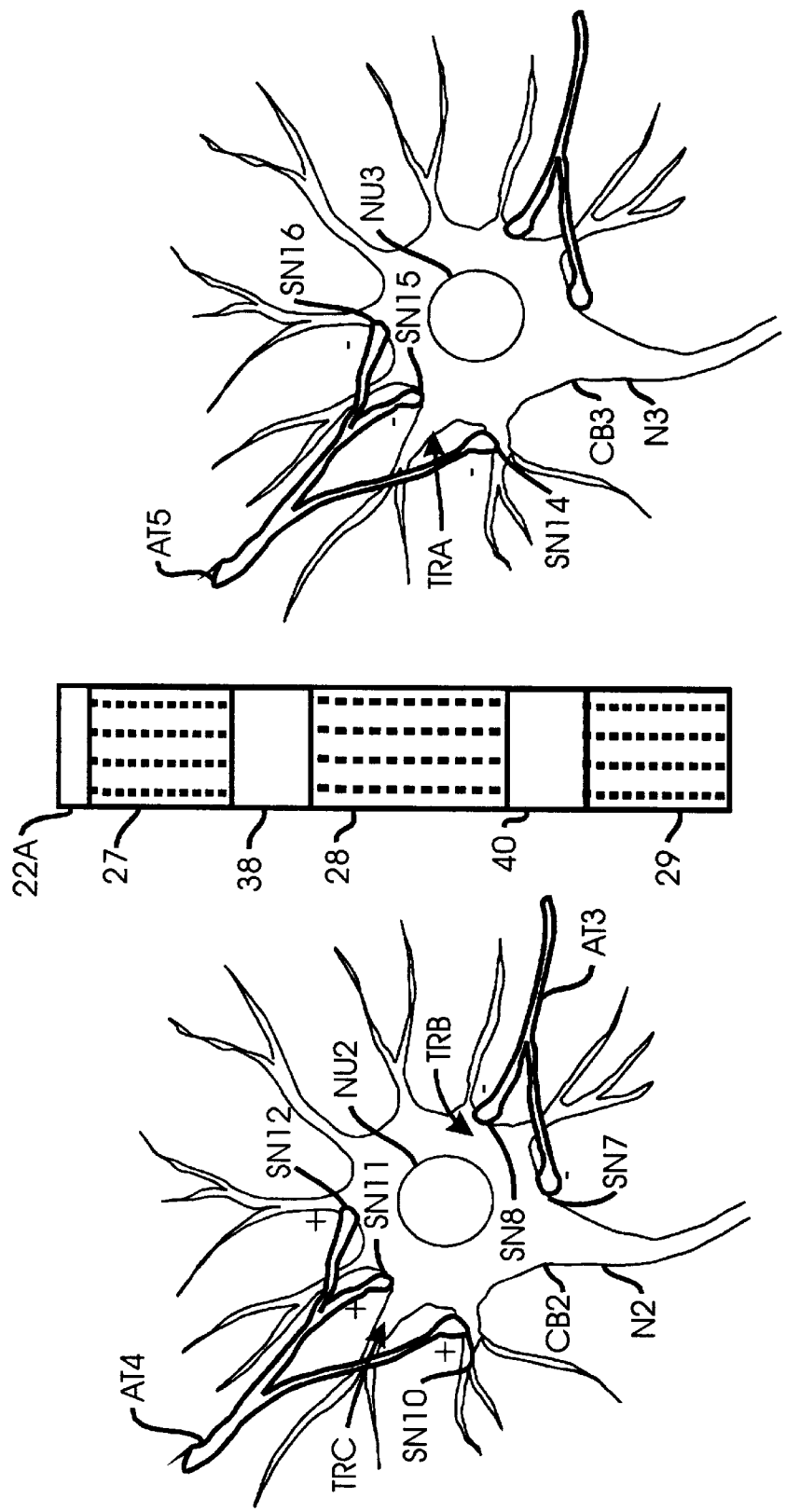

Referring to FIG. 14, a neuron N2 has a cell body CB2 and a nucleus NU2. Neuron N2 can be inhibited by axon terminals AT3 at synapses SN7–SN8 by an inhibitory neurotransmitter TRB and can be excited by axon terminals AT4 at synapses SN10–SN12 by an excitatory neurotransmitter TRC.

A neuron N3 has a cell body CB3 and a nucleus NU3. Neuron N3 can be inhibited by axon terminals AT5 at synapses SN14-SN16 by an inhibitory neurotransmitter TRA. Portions 27–29 of tube 22A are used to infuse into the region of neurons N2 and N3 one or more of the following agents: an agonist of transmitter TRA, an agent to block the reuptake of transmitter TRA or an agent to block a degradative enzyme for transmitter TRA. Each of these agents hyperpolarize neuron N3 and increase the potential threshold required to create action potentials in neuron N3. Therefore, neuron N2 can be selectively activated by electrodes 38 and 40 so that an action potential is created in neuron N2 without creating an action potential in neuron N3.

Selective activation of neuron N2 also can be achieved by infusing into the region of neurons N2 and N3 one or more of the following agents: an agonist for transmitter TRC, an agent to block the reuptake of transmitter TRC, an agent to block the degrading enzyme for transmitter TRC, an antagonist for transmitter TRB, an agent to enhance the reuptake of transmitter TRB or a degrading enzyme for transmitter TRB. The agents can be infused separately or together in a cocktail. Such infusion leads to partial depolarization of neuron N2 and to a reduced threshold to stimulation by electrodes 38 and 40. That is, after infusion, the amplitude of stimulation required to create action potentials in neuron N2 is reduced compared to the time period before infusion, making it easier to electrically stimulate neuron N2 relative to neuron N3.

Figure 15:
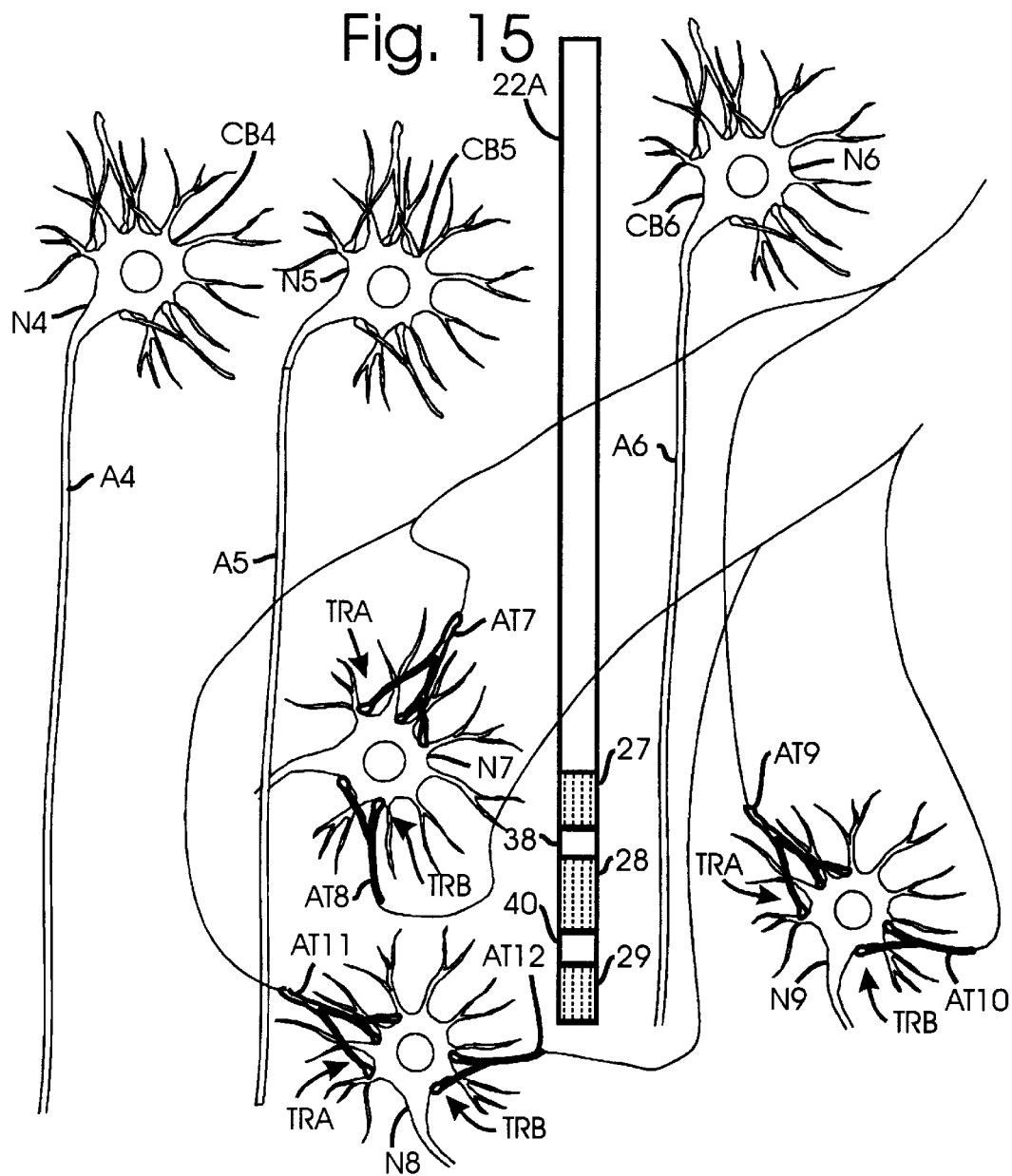

Referring to FIG. 15, neurons N4–N6 have cells bodies CB4–CB6, respectively, and axons A4–A6, respectively, which are long fibers of passage that typically pass through white tissue in the spinal cord or brain. Cell bodies CB4–CB6 are located at portions of the body somewhat remote from infusion portions 27–29 and electrodes 38 and 40. However, a portions of axons A4–A6 pass in the region of infusion portions 27–29 and electrodes 38 and 40. Neurons N7–N9 have cell bodies that are located in the region of infusion portions 27–29 and electrodes 38 and 40. Neuron N7 can be inhibited at axon terminals AT7 by an inhibitory neurotransmitter TRA and excited at axon terminals AT8 by an excitatory neurotransmitter TRB; neuron N9 can be inhibited at axon terminals AT9 by inhibitory neurotransmitter TRA and excited at axon terminals AT10 by excitatory neurotransmitter TRB; and neuron N8 can be inhibited at axon terminals AT11 by inhibitory neurotransmitter TRA and excited at axon terminals AT12 by an excitatory neurotransmitter TRB. Portions 27–29 are used to infuse an agonist of transmitter TRA, a reuptake blocker to transmitter TRA, a degrading enzyme blocker to transmitter TRA or an antagonist or degrading enzyme to transmitter TRB to raise the stimulation threshold of neurons N7–N9. Neurons N4–N6 are not affected by the infusion and can be selectively activated by stimulation supplied by electrodes 38 and 40.

Figure 16:
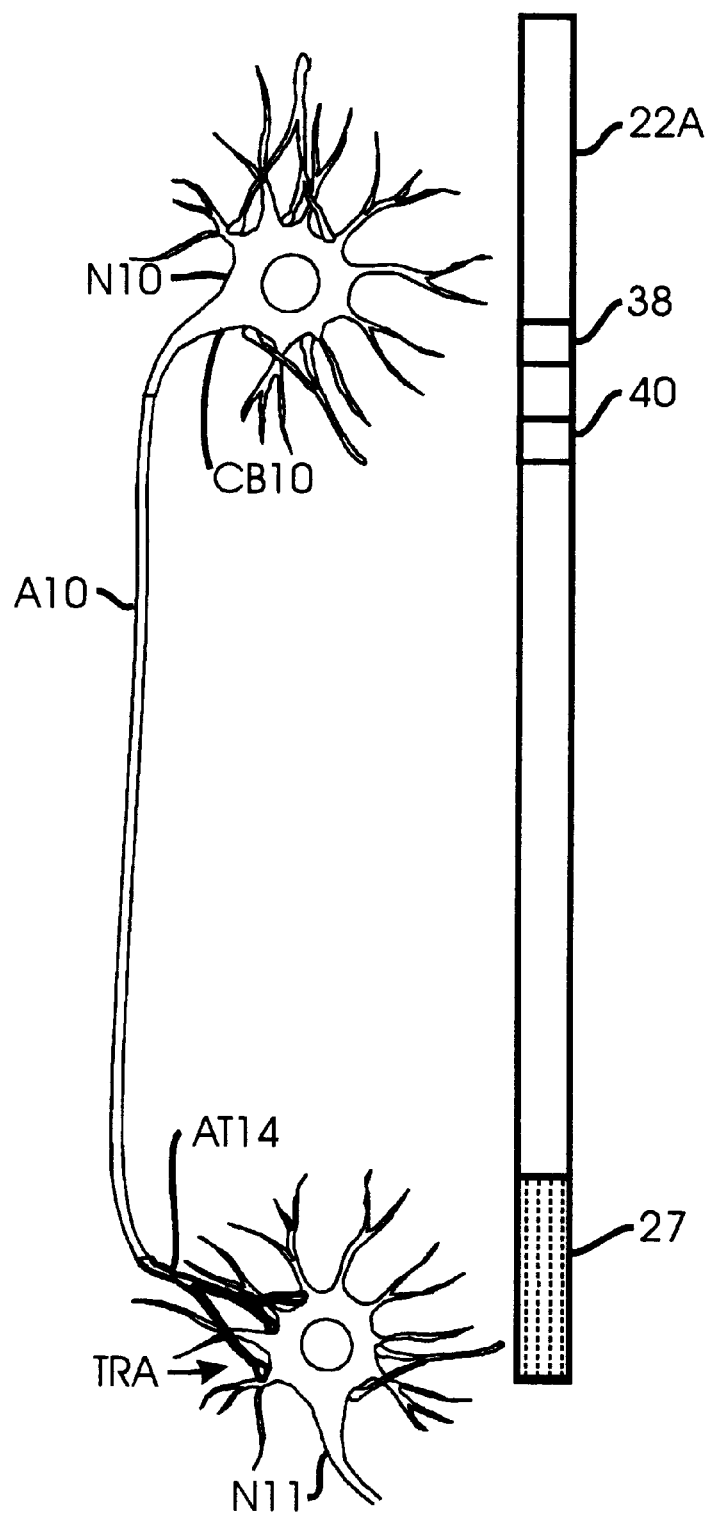

FIG. 16 illustrates a modified form of tube 22A in which infusion portion 27 is located more than 0.01 cm from electrodes 38 and 40 and infusion portions 28–29 have been removed. Neuron N10 has a cell body CB10 and an axon A10 that terminates in axon terminals AT14. A neuron N11 can be excited at axon terminals AT14 by an excitatory neurotransmitter TRA. Electrical stimulation of axon A10 causes the release of transmitter TRA at axon terminal AT14. Portion 27 is used to infuse an agent that blocks a degradative enzyme of transmitter TRA or an agent which blocks the reuptake of transmitter TRA. For each pulse administered by electrodes 38 and 40, the stimulation of neuron N11 is more potent. That is, more action potentials are generated in neuron N11.

Figure 18A:
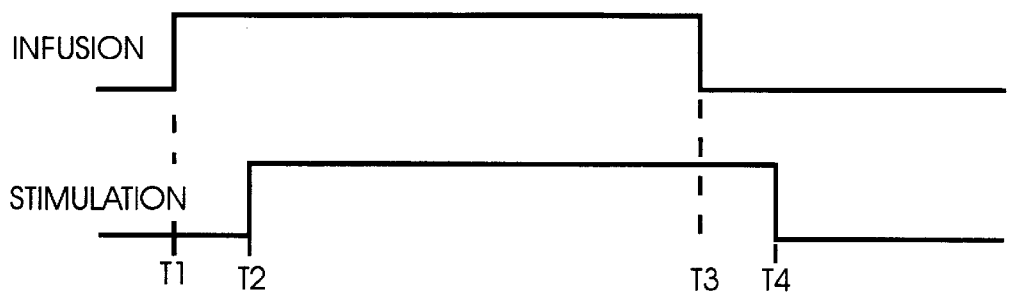
FIGS. 18A–18C are timing diagrams showing the relationship between the administration of drugs and electrical stimulation to neural tissue.
Figure 18B:
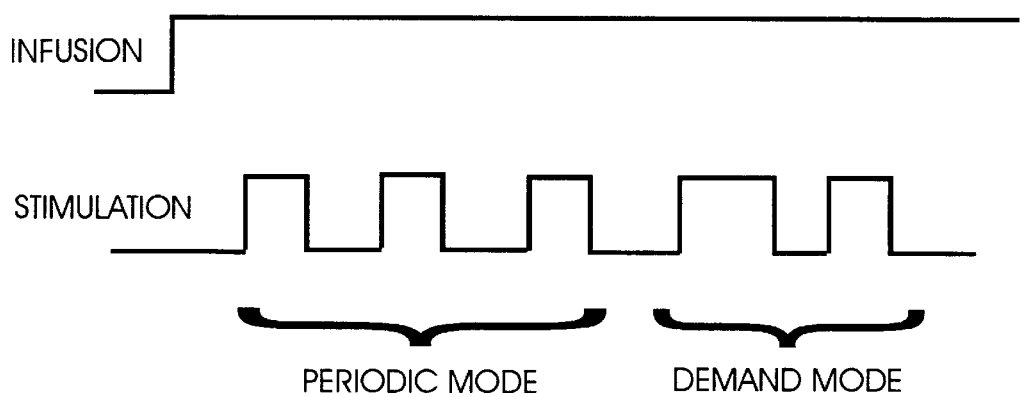
Figure 18C:
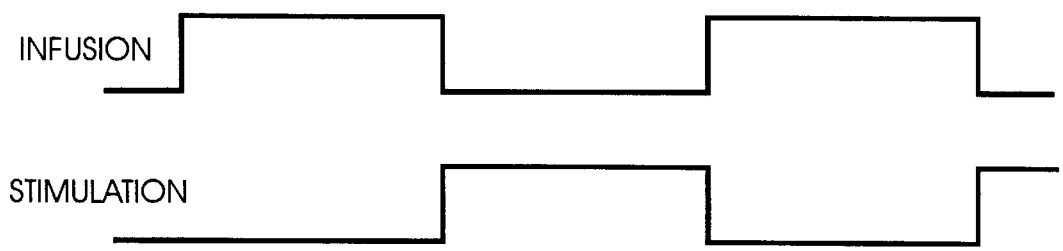

FIG. 18A illustrates various times at which infusion and stimulation can be applied by tube 22A. For example, infusion alone can be applied from time T1 to T2, infusion and stimulation can be both be applied from time T2 to T3, and stimulation alone can be applied from time T3 to T4. This regimen might be used in the case when selective activation of one neuronal population is desired. By beginning the infusion before beginning stimulation during time T1 to T2, the threshold for electrical activation of one population of neurons can be lowered or raised as needed. Another example would be if a precursor molecule, such as L-dopa, is infused to guard against depletion of transmitter substance. The stimulation might be applied periodically during the period of infusion either routinely or in response to sensor or patient generated demand as shown in FIG. 18B. Alternatively, the infusion of an agent to activate a neuronal population might be alternated with application of electrical stimulation of that same population, as shown in FIG. 18C.

Figure 17:
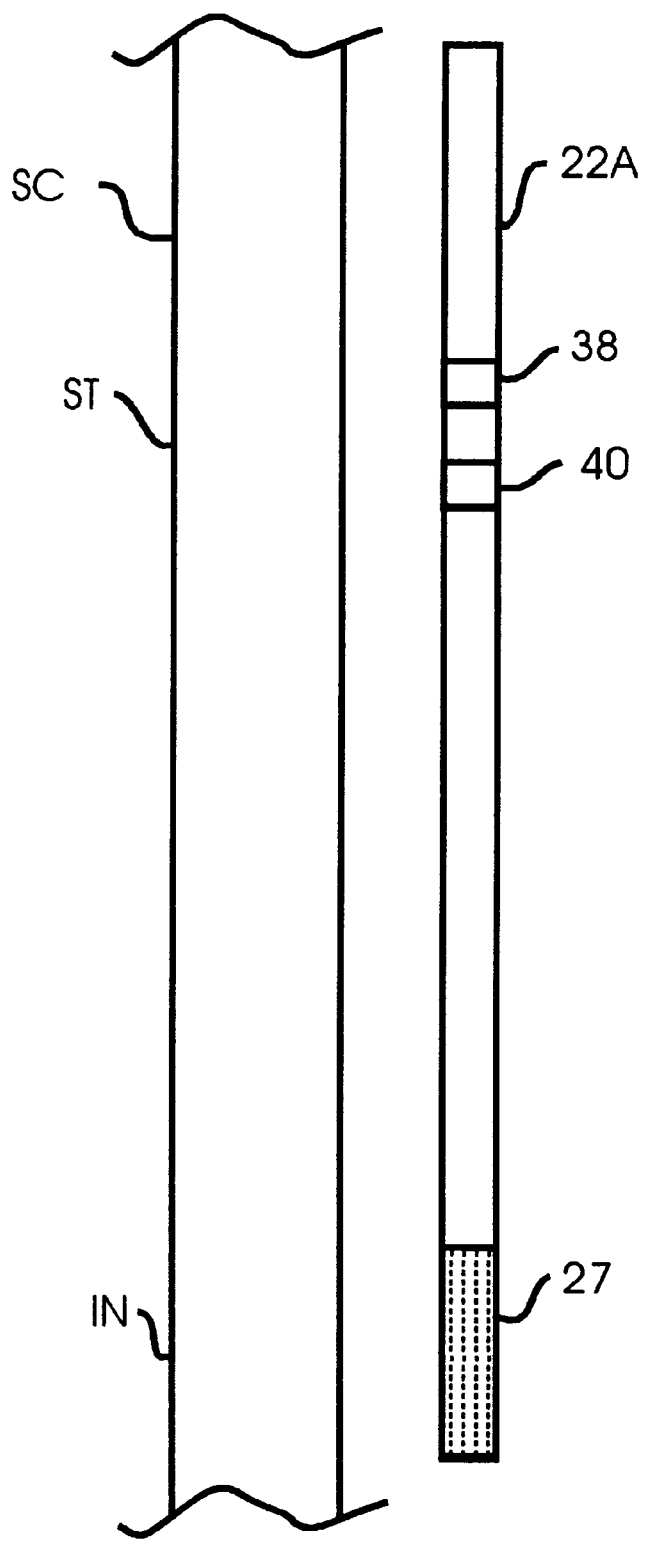

It also is possible to infuse an agent that has an affect upon the neuron population that is not strictly connected in time with the electrical depolarization of the neurons. In this case, the time of application of stimulation and infusion may be completely asynchronous. Or an agent could be infused that diffuses beyond the effects of the electrical stimulation but still has an advantageous effect on the brain independent of the stimulation effects. As an example, FIG. 17 illustrates the same form of tube 22A shown in FIG. 16 implanted adjacent a spinal cord SC. A steroid, or other anti-inflammatory drug, can be infused through portion 27 to reduce inflammation in area IN of the spinal cord, while portion ST, such as the dorsal columns, is electrically stimulated by electrodes 38 and 40 to treat the pain. Alternatively, an antispasmodic could be infused to treat the spasms associated with mechanical back problems while stimulation is applied to the spinal cord to treat the pain.

By using the foregoing techniques for simultaneous drug infusion and electrical stimulation, neural disorders, including motor disorders, can be controlled with a degree of accuracy previously unattainable. Those skilled in that art will recognize that the preferred embodiments may be altered or amended without departing from the true spirit and scope of the invention, as defined in the accompanying claims.

We claim:

1. A method of using one or more drugs to therapeutically treat a neural disorder including a movement disorder over a predetermined time period by means of an implantable pump and a catheter having a proximal end coupled to said pump and a discharge portion for infusing therapeutic dosages of said one or more drugs, as well as a signal generator and at least one implantable electrode having a proximal end and a stimulation portion, said method comprising the steps of:

surgically implanting said electrode so that the stimulation portion lies adjacent a predetermined stimulation site in subdural neural tissue;

surgically implanting said catheter so that the discharge portion lies adjacent a predetermined infusion site in subdural neural tissue;

coupling said proximal end of said electrode to said signal generator;

operating said signal generator to treat said neural disorder by stimulating said stimulation site during at least a portion of said predetermined time period;

operating said pump to treat said neural disorder by discharging a predetermined dosage of said one or more drugs through said discharge portion of said catheter into said infusion site during at least a portion of said predetermined time period, whereby said neural disorder is treated.

2. A method, as claimed in claim 1, wherein said neural disorder is a hyperkinetic disorder, said method further including the step of selecting said stimulation and infusion sites in the brain, wherein said stimulation site and infusion site are from the group consisting of the ventrolateral thalamus (Thal), internal segment of globus pallidus (GPi), substantia nigra pars reticulata (SNr), subthalamic nucleus (STN), external segment of globus pallidus (GPe) and neostriatum, and wherein said stimulation and said discharge reduce thalamic output.

3. A method, as claimed in claim 2, wherein said step of operating said signal generator and said step of operating said pump include the step of decreasing excitement of the thalamus or increasing inhibition of the thalamus.

4. A method, as claimed in claim 3, wherein said step of operating said signal generator and said step of operating said pump include the step of decreasing inhibition or increasing excitation of said internal segment of globus pallidus (GPi), substantia nigra pars reticulata (SNr) or subthalamic nucleus (STN) that inhibit thalamic output.

5. A method, as claimed in claim 3, wherein said step of operating said signal generator and said step of operating said pump include the step of decreasing excitation or increasing inhibition of said external segment of globus pallidus (Gpe).

6. A method, as claimed in claim 1, wherein said steps involve therapeutically treating a hyperkinetic disorder comprising dystonia, ballism, hemiballism, chorea, athetosis, torticollis, or spasticity.

7. A method, as claimed in claim 1, wherein said step of operating said signal generator includes the step of stimulating said stimulation site with pulses having a repetition rate of 2 to 2500 Hz. or more.

8. A method, as claimed in claim 1, wherein said steps involve therapeutically treating a hypokinetic disorder comprising Parkinson's disease, akinesia, rigidity, or bradykinesia.

9. A method, as claimed in claim 1, wherein said neural disorder is a hypokinetic disorder, said method further including the step of selecting said stimulation and infusion sites in the brain, wherein said stimulation site and infusion site are from the group consisting of the ventrolateral thalamus (Thal), internal segment of globus pallidus (GPi), substantia nigra pars reticulata (SNr), subthalamic nucleus (STN), external segment of globus pallidus (GPe) and neostriatum, and wherein said stimulation and said discharge increase thalamic output.

10. A method, as claimed in claim 9, wherein said step of operating said signal generator and said step of operating said pump includes the step of increasing excitement of the thalamus or decreasing inhibition of the thalamus.

11. A method, as claimed in claim 10, wherein said step of operating said signal generator and said step of operating said pump includes the step of increasing inhibition or decreasing excitation of said internal segment of globus pallidus (GPi), substantia nigra pars reticulata (SNr) or subthalamic nucleus (STN) that inhibit thalamic output.

12. A method, as claimed in claim 10, wherein said step of operating said signal generator and said step of operating said pump includes the step of increasing excitation or decreasing inhibition of said external segment of globus pallidus (GPe).

13. A method, as claimed in claim 8, wherein said step of operating said signal generator and said step of operating said pump includes the step of increasing excitement of the thalamus or decreasing inhibition of the thalamus.

14. A method, as claimed in claim 13, wherein said step of operating said signal generator and said step of operating said pump includes the step of increasing inhibition or decreasing excitation of said internal segment of globus pallidus (GPi), substantia nigra pars reticulata (SNr) or subthalamic nucleus (STN) that inhibit thalamic output.

15. A method, as claimed in claim 13, wherein said step of operating said signal generator and said step of operating said pump includes the step of increasing excitation or decreasing inhibition of said external segment of globus pallidus (Gpe).

16. A method, as claimed in claim 1, including the step of selecting said one or more drugs from the group consisting of an antagonist of an inhibitory neurotransmitter acting on said neural tissue, an agonist of an excitatory neurotransmitter acting on said neural tissue, a drug blocking the uptake of said excitatory neurotransmitter, a drug blocking the action of a degradative enzyme of said excitatory neurotransmitter, a degradative enzyme for said inhibitory neurotransmitter and potassium, whereby the amplitude of said stimulation required to create an action potential in said neural tissue is reduced.

17. A method, as claimed in claim 1, wherein said neural tissue comprises a first neural tissue responsive to a first type of neurotransmitter and a second neural tissue responsive to a second type of neurotransmitter, and including the step of applying said one or more drugs to act on said first and second type of neurotransmitters so that said stimulation required to create an action potential in said first neural tissue is reduced compared to said stimulation required to create an action potential in said second neural tissue.

18. A method, as claimed in claim 17, wherein said neural tissue comprises a first neural tissue responsive to a first type of excitatory neurotransmitter and a second neural tissue responsive to a second type of excitatory neurotransmitter, including the step of selecting said one or more drugs from the group consisting of an agonist of said first type of excitatory neurotransmitter acting on said neural tissue, a drug blocking the uptake of said first type of excitatory neurotransmitter, a degradative enzyme for said second type of excitatory neurotransmitter, whereby said stimulation required to create an action potential in said first neural tissue is reduced compared to said stimulation required to create an action potential in said second neural tissue.

19. A method as claimed in claim 17, wherein said neural tissue comprises a first neural tissue responsive to a first type of inhibitory neurotransmitter and a second neural tissue responsive to a second type of inhibitory neurotransmitter, including the step of selecting said one or more drugs from the group consisting of said first type of inhibitory neurotransmitter acting on said neural tissue, a drug blocking the uptake of said second type of inhibitory neurotransmitter, a degradative enzyme for said first type of inhibitory neurotransmitter, whereby said stimulation required to create an action potential in said first neural tissue is reduced compared to said stimulation required to create an action potential in said second neural tissue.

20. A method, as claimed in claim 1, wherein said neural tissue comprises a first neural tissue responsive to a first type of neurotransmitter and a second neural tissue comprising fibers of passage, and including the step of applying said one or more drugs to act on said first neural tissue so that said stimulation required to create an action potential in said first neural tissue is raised, whereby said fibers of passage can be stimulated without creating action potentials in said first neural tissue.

21. A method, as claimed in claim 1, wherein said neural tissue comprises a first nerve comprising an axon that terminates in axon terminals and a second nerve comprising a cell body including a receiving cell that communicates with said axon terminals across a synapse by means of a neurotransmitter, wherein said stimulation site is adjacent said axon and wherein said infusion site is adjacent said synapse, and including the step of selecting said one or more drugs from the group consisting of a blocker of a degradative enzyme of said neurotransmitter and a drug blocking the reuptake of said neurotransmitter, whereby the said stimulation of said axon results in increased excitement of said second nerve.

22. A method as claimed in claim 1, wherein said neutral tissue is a spinal cord, wherein the step of implanting said catheter includes locating said infusion site adjacent a first predetermined portion of said spinal cord and wherein the step of implanting said electrode includes locating said stimulation site adjacent a second predetermined portion of said spinal cord displaced from said predetermined portion.

23. A method, as claimed in claim 1, comprising the additional steps of:
generating a sensor signal related to activity resulting from said neural disorder; and
regulating said steps operating said signal generator and operating said pump in response to said sensor signal.

24. A method, as claimed in claim 23, wherein said step of generating is achieved using a motion detector.

25. A method, as claimed in claim 23, wherein said step of generating is achieved using means for detecting changes in electromagnetic waves generated by muscle or neural tissue.

26. A method, as claimed in claim 23, wherein said step of regulating is achieved using a microprocessor.

27. A system using one or more drugs to therapeutically treat a neural disorder comprising in combination:
an implantable pump;
a catheter having a proximal end coupled to said pump and a discharge portion adapted to infuse a therapeutic dosage of said one or more drugs into a predetermined infusion site in subdural neural tissue;
an implantable signal generator;
an implantable electrode having a proximal end coupled to said signal generator and a stimulation portion adapted to stimulate a predetermined stimulation site in said subdural neural tissue;
a sensor for generating a sensor signal related to activity resulting from said neural disorder; and
control means responsive to said sensor signal for regulating said stimulation and said therapeutic dosage, whereby said neural disorder is treated.

28. A system, as claimed in claim 27, wherein said sensor comprises means for detecting changes in electromagnetic waves generated by muscle or neural tissue.

29. A system, as claimed in claim 27, wherein said control means comprises a microprocessor.

30. A system using one or more drugs to therapeutically treat a neural disorder comprising in combination:
an implantable pump;
a catheter having a proximal end coupled to said pump and a discharge portion adapted to infuse a therapeutic dosage of said one or more drugs into a predetermined infusion site in subdural neural tissue;
an implantable signal generator;
an implantable electrode having a proximal end coupled to said signal generator and a stimulation portion adapted to stimulate a predetermined stimulation site in subdural neural tissue;
a sensor for generating a sensor signal related to activity resulting from said neural disorder, said sensor having a motion detector; and
control means responsive to said sensor signal for regulating said stimulation and said therapeutic dosage, whereby said neural disorder is treated.

31. A system using one or more drugs to therapeutically treat a neural disorder comprising in combination:
an implantable pump;
a catheter having a proximal end coupled to said pump and a discharge portion adapted to infuse a therapeutic dosage of said one or more drugs into a predetermined infusion site in subdural neural tissue;
an implantable signal generator;
an implantable electrode having a proximal end coupled to said signal generator and a stimulation portion adapted to stimulate a predetermined stimulation site in subdural neural tissue;
a sensor for generating a sensor signal related to activity resulting from said neural disorder; and
control means responsive to said sensor signal for regulating said stimulation and said therapeutic dosage, said control means having an electrical filter, whereby said neural disorder is treated.

32. A system using one or more drugs to therapeutically treat a hyperkinetic or hypokinetic disorder comprising in combination:
an implantable pump;

a catheter having a proximal end coupled to said pump and a discharge portion adapted to infuse a therapeutic dosage of said one or more drugs into a predetermined infusion site in subdural neural tissue;

an implantable signal generator;

an implantable electrode having a proximal end coupled to said signal generator and a stimulation portion adapted to stimulate a predetermined stimulation site in subdural neural tissue;

a hyperkinetic or hypokinetic disorder sensor for generating a sensor signal related to activity resulting from said hyperkinetic or hypokinetic disorder; and control means responsive to said sensor signal for regulating said stimulation and said therapeutic dosage, whereby said neural disorder is treated.

33. A method of using one or more drugs to therapeutically treat a neural disorder over a predetermined time period by means of an implantable pump and a catheter having a proximal end coupled to said pump and a discharge portion for infusing therapeutic dosages of said one or more drugs, as well as a signal generator and an implantable electrode having a proximal end and a stimulation portion, said method comprising the steps of:

surgically implanting said electrode so that the stimulation portion lies adjacent a predetermined stimulation site in neural tissue in a brain of a body;

surgically implanting said catheter so that the discharge portion lies adjacent a predetermined infusion site in neural tissue in a brain of a body;

coupling said proximal end of said electrode to said signal generator;

operating said signal generator to stimulate said stimulation site during at least a portion of said predetermined time period;

operating said pump to discharge a predetermined dosage of said one or more drugs through said discharge portion of said catheter into said infusion site during at least a portion of said predetermined time period, whereby said neural disorder is treated.

34. A system using one or more drugs to therapeutically treat a neural disorder comprising in combination:

an implantable pump;

a catheter for implantation within a brain of a body having a proximal end coupled to said pump and a discharge portion adapted to infuse a therapeutic dosage of said one or more drugs into a predetermined infusion site in neural tissue in said brain;

an implantable signal generator;

an implantable electrode for implantation within said brain having a proximal end coupled to said signal generator and a stimulation portion adapted to stimulate a predetermined stimulation site in neural tissue in said brain;

a sensor for generating a sensor signal related to activity resulting from said neural disorder; and control means responsive to said sensor signal for regulating said stimulation and said therapeutic dosage, whereby said neural disorder is treated.

35. A method of using one or more drugs to therapeutically treat a neural disorder including a movement disorder over a predetermined time period by means of an implantable pump and a catheter having a proximal end coupled to said pump and a discharge portion for infusing therapeutic dosages of said one or more drugs, as well as a signal generator and at least one implantable electrode having a proximal end and a stimulation portion, said method comprising the steps of:

surgically implanting said electrode so that the stimulation portion lies adjacent a predetermined stimulation site in subdural neural tissue;

surgically implanting said catheter so that the discharge portion lies adjacent a predetermined infusion site in subdural neural tissue;

coupling said proximal end of said electrode to said signal generator;

detecting a symptom of said neural disorder;

operating said signal generator to treat said neural disorder by stimulating said stimulation site during at least a portion of said predetermined time period;

operating said pump to treat said neural disorder by discharging a predetermined dosage of said one or more drugs through said discharge portion of said catheter into said infusion site during at least a portion of said predetermined time period, whereby said neural disorder is treated.

36. A method, as claimed in claim 35, wherein said neural disorder is a hyperkinetic disorder, said method further including the step of selecting said stimulation and infusion sites in the brain, wherein said stimulation site and infusion site are from the group consisting of the ventrolateral thalamus (Thal), internal segment of globus pallidus (GPi), substantia nigra pars reticulata (SNr), subthalamic nucleus (STN), external segment of globus pallidus (GPe) and neostriatum, and wherein said stimulation and said discharge reduce thalamic output.

37. A method, as claimed in claim 35, wherein said steps involve therapeutically treating a hyperkinetic disorder comprising dystonia, ballism, hemiballism, chorea, athetosis, torticollis, or spasticity.

38. A method, as claimed in claim 36, wherein said step of operating said signal generator and said step of operating said pump include the step of decreasing excitement of the thalamus or increasing inhibition of the thalamus.

39. A method, as claimed in claim 38, wherein said step of operating said signal generator and said step of operating said pump include the step of decreasing inhibition or increasing excitation of said internal segment of globus pallidus (GPi), substantia nigra pars reticulata (SNr) or subthalamic nucleus (STN) that inhibit thalamic output.

40. A method, as claimed in claim 38, wherein said step of operating said signal generator and said step of operating said pump include the step of decreasing excitation or increasing inhibition of said external segment of globus pallidus (Gpe).

41. A method, as claimed in claim 35, wherein said step of operating said signal generator includes the step of stimulating said stimulation site with pulses having a repetition rate of 2 to 2500 Hz. or more.

42. A method, as claimed in claim 35, wherein said neural disorder is a hypokinetic disorder, said method further including the step of selecting said stimulation and infusion sites in the brain, wherein said stimulation site and infusion site are from the group consisting of the ventrolateral thalamus (Thal), internal segment of globus pallidus (GPi), substantia nigra pars reticulata (SNr), subthalamic nucleus (STN), external segment of globus pallidus (GPe) and neostriatum, and wherein said stimulation and said discharge increase thalamic output.

43. A method, as claimed in claim 35, wherein said steps involve therapeutically treating a hypokinetic disorder comprising Parkinson's disease, akinesia, rigidity, or bradykinesia.

44. A method, as claimed in claim 35, including the step of selecting said one or more drugs from the group consisting of an antagonist of an inhibitory neurotransmitter acting on said neural tissue, an agonist of an excitatory neurotransmitter acting on said neural tissue, a drug blocking the uptake of said excitatory neurotransmitter, a drug blocking the action of a degradative enzyme of said excitatory neurotransmitter, a degradative enzyme for said inhibitory neurotransmitter and potassium, whereby the amplitude of said stimulation required to create an action potential in said neural tissue is reduced.

45. A method, as claimed in claim 35, wherein said neural tissue comprises a first neural tissue responsive to a first type of neurotransmitter and a second neural tissue responsive to a second type of neurotransmitter, and including the step of applying said one or more drugs to act on said first and second type of neurotransmitters so that said stimulation required to create an action potential in said first neural tissue is reduced compared to said stimulation required to create an action potential in said second neural tissue.

46. A method, as claimed in claim 45, wherein said neural tissue comprises a first neural tissue responsive to a first type of excitatory neurotransmitter and a second neural tissue responsive to a second type of excitatory neurotransmitter, including the step of selecting said one or more drugs from the group consisting of an agonist of said first type of excitatory neurotransmitter acting on said neural tissue, a drug blocking the uptake of said first type of excitatory neurotransmitter, a degradative enzyme for said second type of excitatory neurotransmitter, whereby said stimulation required to create an action potential in said first neural tissue is reduced compared to said stimulation required to create an action potential in said second neural tissue.

47. A method as claimed in claim 45, wherein said neural tissue comprises a first neural tissue responsive to a first type of inhibitory neurotransmitter and a second neural tissue responsive to a second type of inhibitory neurotransmitter, including the step of selecting said one or more drugs from the group consisting of said first type of inhibitory neurotransmitter acting on said neural tissue, a drug blocking the uptake of said second type of inhibitory neurotransmitter, a degradative enzyme for said first type of inhibitory neurotransmitter, whereby said stimulation required to create an action potential in said first neural tissue is reduced compared to said stimulation required to create an action potential in said second neural tissue.

48. A method, as claimed in claim 35, wherein said neural tissue comprises a first neural tissue responsive to a first type of neurotransmitter and a second neural tissue comprising fibers of passage, and including the step of applying said one or more drugs to act on said first neural tissue so that said stimulation required to create an action potential in said first neural tissue is raised, whereby said fibers of passage can be stimulated without creating action potentials in said first neural tissue.

49. A method, as claimed in claim 35, wherein said neural tissue comprises a first nerve comprising an axon that terminates in axon terminals and a second nerve comprising a cell body including a receiving cell that communicates with said axon terminals across a synapse by means of a neurotransmitter, wherein said stimulation site is adjacent said axon and wherein said infusion site is adjacent said synapse, and including the step of selecting said one or more drugs from the group consisting of a blocker of a degradative enzyme of said neurotransmitter and a drug blocking the reuptake of said neurotransmitter, whereby the said stimulation of said axon results in increased excitement of said second nerve.

50. A method as claimed in claim 35, wherein said neutral tissue is a spinal cord, wherein the step of implanting said catheter includes locating said infusion site adjacent a first predetermined portion of said spinal cord and wherein the step of implanting said electrode includes locating said stimulation site adjacent a second predetermined portion of said spinal cord displaced from said predetermined portion.

51. A method, as claimed in claim 35, comprising the additional steps of:
generating a sensor signal related to activity resulting from said neural disorder; and
regulating said steps operating said signal generator and operating said pump in response to said sensor signal.

52. A method, as claimed in claim 50, wherein said step of generating is achieved using a motion detector.

53. A method, as claimed in claim 50, wherein said step of generating is achieved using means for detecting changes in electromagnetic waves generated by muscle or neural tissue.

54. A method, as claimed in claim 50, wherein said step of regulating is achieved using a microprocessor.

55. A method of using one or more drugs to therapeutically treat a neural disorder over a predetermined time period by means of an implantable pump and a catheter having a proximal end coupled to said pump and a discharge portion for infusing therapeutic dosages of said one or more drugs, as well as a signal generator and at least one implantable electrode having a proximal end and a stimulation portion, said method comprising the steps of:
surgically implanting said electrode so that the stimulation portion lies adjacent a predetermined stimulation site in neural tissue in a brain of a body;
surgically implanting said catheter so that the discharge portion lies adjacent a predetermined infusion site in neural tissue in a brain of a body;
coupling said proximal end of said electrode to said signal generator;
detecting a symptom of said neural disorder;
operating said signal generator to treat said neural disorder by stimulating said stimulation site during at least a portion of said predetermined time period;
operating said pump to discharge a predetermined dosage of said one or more drugs through said discharge portion of said catheter into said infusion site during at least a portion of said predetermined time period, whereby said neural disorder is treated.

56. A method of using at least one drug to therapeutically treat a movement disorder by means of an implantable pump and a catheter having a proximal end coupled to said pump and a discharge portion for infusing therapeutic dosages of said at least one drug, as well as a signal generator and at least one implantable electrode having a proximal end and a stimulation portion, said method comprising the steps of:
surgically implanting said electrode so that the stimulation portion lies adjacent a predetermined stimulation site;
surgically implanting said catheter so that the discharge portion lies adjacent a predetermined infusion site;
coupling said proximal end of said electrode to said signal generator;
detecting a symptom of said movement disorder;
operating said signal generator to treat said movement disorder by stimulating said stimulation site; and
operating said pump to treat said movement disorder by discharging a predetermined dosage of said at least one drug through said discharge portion of said catheter into said infusion site,
whereby said movement disorder is treated.

* * * * *

UNITED STATES PATENT AND TRADEMARK OFFICE
CERTIFICATE OF CORRECTION

PATENT NO. : 6,094,598
DATED : July 25, 2000
INVENTOR(S) : Dennis D. Elsberry, Mark T. Rise, Gary W. King It is certified that error appears in the above-indentified patent and that said Letters Patent is hereby corrected as shown below:

ON THE TITLE PAGE
Item [73] Assignee: "Medtronics, Inc." should be "Medtronic, Inc."

at Column 6, Table I, under EFFECT, the first word "increase" should be deleted.

at Column 11 Table V, under EFFECT, "INCREASE OF GPe should read - - INCREASE INHIBITION OF GPe- -.

Signed and Sealed this

Twenty-seventh Day of March, 2001

Attest:

NICHOLAS P. GODICI

Attesting Officer        Acting Director of the United States Patent and Trademark Office